United States Patent
Riskin et al.

(10) Patent No.: US 9,740,665 B2
(45) Date of Patent: Aug. 22, 2017

(54) SYSTEMS AND METHODS FOR PROCESSING PATIENT INFORMATION

(71) Applicant: HEALTH FIDELITY, INC., Menlo Park, CA (US)

(72) Inventors: Daniel Riskin, Palo Alto, CA (US); Carol Friedman, Palo Alto, CA (US)

(73) Assignee: Health Fidelity, Inc., San Mateo, CA (US)

( * ) Notice: Subject to any disclaimer, the term of this patent is extended or adjusted under 35 U.S.C. 154(b) by 494 days.

(21) Appl. No.: 14/333,127

(22) Filed: Jul. 16, 2014

(65) Prior Publication Data

US 2014/0330586 A1    Nov. 6, 2014

Related U.S. Application Data

(63) Continuation of application No. 14/372,562, filed as application No. PCT/US2013/055591 on Aug. 19, 2013.

(60) Provisional application No. 61/684,733, filed on Aug. 18, 2012.

(51) Int. Cl.
*G06F 17/21*  (2006.01)
*G06F 17/27*  (2006.01)
*G06F 19/00*  (2011.01)
*G06Q 50/24*  (2012.01)

(52) U.S. Cl.
CPC .......... *G06F 17/211* (2013.01); *G06F 17/277* (2013.01); *G06F 17/2765* (2013.01); *G06F 19/322* (2013.01); *G06F 19/3487* (2013.01); *G06Q 50/24* (2013.01)

(58) Field of Classification Search
CPC ............................ G06F 17/277; G06F 17/285
See application file for complete search history.

(56) References Cited

U.S. PATENT DOCUMENTS

| | | | | |
|---|---|---|---|---|
| 6,182,029 B1 * | 1/2001 | Friedman | ............ | G06F 17/2705 704/9 |
| 6,915,254 B1 * | 7/2005 | Heinze | .................... | G06F 17/27 382/225 |
| 2003/0046114 A1 * | 3/2003 | Davies | ................... | G06Q 10/10 705/3 |
| 2007/0299651 A1 * | 12/2007 | Koll | ...................... | G06F 17/211 704/9 |

(Continued)

FOREIGN PATENT DOCUMENTS

WO    WO2012094422 A2    7/2012

OTHER PUBLICATIONS

Aronson, Alan R., et al. "The NLM indexing initiative's medical text indexer." Medinfo 11.Pt 1 (2004): 268-72.*

(Continued)

*Primary Examiner* — Brian Albertalli
(74) *Attorney, Agent, or Firm* — Royse Law Firm, PC

(57) ABSTRACT

Systems and methods described herein are for transforming narrative content into structured output. In some embodiments the narrative content is processed using a natural language processing (NLP) engine and a clinical model. The structured output can include a section, a clinical assertion, and a plurality of elements, wherein the elements may include section elements and clinical assertion elements that annotate the section and clinical assertions respectively. The elements can be labeled based on the clinical model.

11 Claims, 6 Drawing Sheets

(56) References Cited

U.S. PATENT DOCUMENTS

| | | | |
|---|---|---|---|
| 2008/0294692 A1 | | 11/2008 | Angell et al. |
| 2010/0010804 A1* | | 1/2010 | Friedman ............... G06F 17/277 704/9 |
| 2012/0065987 A1 | | 3/2012 | Farooq et al. |
| 2012/0084074 A1* | | 4/2012 | Chronister ........ G06F 17/30616 704/9 |
| 2012/0231959 A1 | | 9/2012 | Elton et al. |
| 2013/0046529 A1* | | 2/2013 | Grain .................... G06F 17/289 704/2 |
| 2014/0142924 A1* | | 5/2014 | Friedman ................ G06F 17/21 704/9 |

OTHER PUBLICATIONS

Friedman, Carol, et al. "Automated encoding of clinical documents based on natural language processing." Journal of the American Medical Informatics Association 11.5 (2004): 392-402.*

Aronson, Alan R., and François-Michel Lang. "An overview of MetaMap: historical perspective and recent advances." Journal of the American Medical Informatics Association 17.3 (2010): 229-236.*

Friedman, Carol, et al. "Representing information in patient reports using natural language processing and the extensible markup language." Journal of the American Medical Informatics Association 6.1 (1999): 76-87.*

Friedman, Carol. "A broad-coverage natural language processing system." Proceedings of the AMIA Symposium. American Medical Informatics Association, 2000.*

Friedman, Carol. "Towards a comprehensive medical language processing system: methods and issues." Proceedings of the AMIA annual fall symposium. American Medical Informatics Association, 1997.*

Rindflesch, Thomas C. "Integrating natural language processing and biomedical domain knowledge for increased information retrieval effectiveness." Proc 5th Annual Dual-use Technologies and Applications Conference. 1995.*

Chapman, Wendy W., David Chu, and John N. Dowling. "ConText: An algorithm for identifying contextual features from clinical text." Proceedings of the Workshop on BioNLP 2007: Biological, Translational, and Clinical Language Processing. Association for Computational Linguistics, 2007.*

Qamar, Rahil, and Alan Rector. "Most: A system to semantically map clinical model data to snomed-ct." In the proceedings of Semantic Mining Conference on SNOMED-CT. 2006.*

Sevenster, Merlijn, Rob Van Ommering, and Yuechen Qian. "Automatically correlating clinical findings and body locations in radiology reports using MedLEE." Journal of digital imaging 25.2 (2012): 240-249.*

Meystre, Stephane, and Peter J. Haug. "Automation of a problem list using natural language processing." BMC medical informatics and decision making 5.1 (2005): 30.*

U.S. Appl. No. 14/066,313, Riskin, Methods for Processing Clinical Information, filed Oct. 29, 2013.

U.S. Appl. No. 14/066,409, Riskin, Clinical Information Processing, filed Oct. 29, 2013.

U.S. Appl. No. 14/372,562, Riskin, Systems and Methods for Processing Patient Information, filed Jul. 16, 2014.

U.S. Appl. No. 14/003,790, Riskin, Systems and Methods for Processing Patient Data History, filed Sep. 6, 2013.

U.S. Appl. No. 13/929,236, Riskin, Voice Based System and Method for Data Input, filed Jun. 27, 2013.

PCT Application No. PCT/US13/55591, International Search Report and Written Opinion, issued Feb. 18, 2014.

PCT Application No. PCT/US13/67283, International Search Report and Written Opinion, issued Aug. 22, 2014.

\* cited by examiner

SYSTEMS AND METHODS FOR PROCESSING PATIENT INFORMATION

CROSS REFERENCE TO RELATED APPLICATIONS

This application is a continuation of U.S. patent application Ser. No. 14/372,562 filed on Jul. 16, 2014 which is a 35 U.S.C. 371 national stage filing from International Application No. PCT/US13/055,591 filed Aug. 19, 2013 which claims priority to and benefit of U.S. Provisional Patent Application Ser. No. 61/684,733 filed Aug. 18, 2012. This application is related to PCT Patent Application No. PCT/US12/27767, titled "SYSTEMS AND METHODS FOR PROCESSING PATIENT HISTORY DATA", filed on Mar. 5, 2012 which is herein incorporated by reference. All publications and patent applications mentioned in this specification are herein incorporated by reference in their entirety to the same extent as if each individual publication or patent application was specifically and individually indicated to be incorporated by reference.

FIELD

Described herein are systems and methods for processing unstructured healthcare data to make that content powerful and rapid to consume. In some embodiments, the systems and methods described herein may be utilized with electronic health records, data warehouses, or processing of individual patient history data.

BACKGROUND

Information in healthcare is all around us and comes in many different forms. In medical record systems today, only about 20% of data are structured, also known as discrete or machine readable. Information that is not structured is ignored or unusable in conventional processes designed to improve care or reduce costs. This is often referred to as a big data problem.

All quality improvement and cost reduction efforts are founded on the same paradigm: measure, intervene, and measure again. The measurement steps, often called quality measures, require significant individual and population based patient data. Whether the data are originally collected through or for revenue cycle management, transcription, electronic health record (EHR), compliance, analytics, or other efforts, the ultimate goal of data collection in healthcare is improved quality, reduced costs, or both.

Current methods of data extraction from the healthcare workflow are typically manual. The physician may use dropdowns or textboxes in an application to code a medical problem or a billing coder may review a chart and assign billing codes. A quality team may be tasked with seeing every patient every day to manually document quality measures. The processes of data extraction in healthcare are slow, expensive, prone to error, and often ineffective. A "coder" is a person that reviews medical data and identifies a corresponding medical code.

As data flow through to systems, designed to improve care or reduce costs, whether they are analytics, compliance, or otherwise based, the underlying quality of data determine the efficacy of the efforts. Conventionally, the data introduced into the system have come from insurance claims data, administrative data, and discrete EHR data, with minimal use of what is known as unstructured data. Unstructured data in healthcare is primarily the medical narratives captured on every patient encounter. Where an encounter may lead to a full page narrative note to document the visit, the coded portion may be 3 or 4 ICD-9 codes. The massive gap in content in a one page narrative note versus 3-4 codes represents a large portion of the gap between the 80% of unstructured data and 20% of discrete data in healthcare. There has been criticism that while the large majority of meaningful information is captured daily in medical narratives, this content is rarely used for quality improvement. The health system needs coded data rather than unstructured medical narratives to address revenue capture, quality improvement, analytics, compliance, interoperability, and countless other application market segments. Thus, a manual system is built up and maintained to produce these discrete and coded data. The process leads to double work, where a narrative is recorded to describe important patient information and a manual coding step is added from provider, coder, quality team, or other personnel to discretely record much of the same information. Even manually coding 3-4 items, documentation time can be doubled from previous systems where only the narrative was required. It is becoming increasingly clear that manual coding is not scalable.

Use of the 80% of unstructured data in healthcare can potentially power a new generation of applications to improve care and reduce costs. It can support two of the three critical steps in healthcare quality improvement of measure, intervene, and measure again. Unfortunately, the technology to extract this information and make it meaningful is limited. If effective and easy to use systems and methods had the capability of extracting the knowledge incorporated within large stores and ongoing data collection of unstructured clinical data, the benefit would be tremendous. By utilizing this knowledge, not only would the need for manual processes be abated, but also the full breadth of clinical content would be available to address quality and costs. Care could be improved and cost reduced through disease management, population health, local and regional quality improvement, efficiency programs, research, comparative effectiveness, and other healthcare applications and systems, all powered by robust processed narrative data.

There is a need for systems and methods that provide for improved data structuring, including data extraction and understanding. But, the need does not end with a single application. Rather, if usage of narrative data is to power a new generation of application in multiple segments of healthcare, the output should be easily integrated and not solely customized for a single application. In order for processed narrative, or unstructured, data to be properly utilized, there is a need for systems and methods that transform narrative content into highly annotated documents that are clearly organized and easy to consume at a programmatic level. As healthcare applications become more modularized, just as other information technology markets and segments have done in recent decades, data extraction engines will need to integrate with multiple types of applications, such as end-user applications, data warehouses, and other content sources and care interventions within healthcare. Allowing for independent and modularized best-of-breed technologies is a time proven way to stimulate innovation and increase the speed of development of powerful applications.

For use of unstructured data in healthcare, the processed unstructured data should be as easy to consume as discrete data entered manually by the provider, coder, quality team, or other data entry personnel. The computer should address the needs of the people rather than healthcare personnel addressing the needs of the computer. At a conceptual level, this output should be easy to consume. Currently, the most programmatically easy to consume output in healthcare is discrete manually tagged concepts, either tagged by the physician or billing coder using dropdowns, text boxes, or check boxes, and ultimately stored as an annotated data element. To provide similarly usable content, unstructured data technologies would ideally model this output, at best using clear clinical modeling and schema-based output to define where individual information will reside and how it can be used. Making automatically structured narrative as easy to consume programmatically as discrete data requires extensive technology expertise and innovation.

Thus, there is a need in the field of processing healthcare data, and more specifically the field of processing electronic narrative content, for new and improved data structuring systems and methods for transforming a narrative note into a highly annotated document that is clearly organized and easily retrievable by other applications. Clear clinical model, schema, and terminology output can support bringing automatically processed unstructured data in line with the quality and usability of discretely documented data elements.

The information required by most healthcare applications is known. There is a need for systems and methods to output clear representations of unstructured narrative data within a modeled, schema-driven, elemental, and coded approach.

When made available, a robust data infrastructure built around structuring narrative content can allow narrative content to power a broad range of applications, foregoing or supplementing manually entered discrete data and addressing needs in quality analytics, reporting compliance, transcription, electronic health record, interoperability, revenue cycle management, and other applications. Described herein are devices, systems and methods that address the problems and meet the identified needs described above.

SUMMARY OF THE DISCLOSURE

Described herein are systems and methods for processing data. In general, methods described herein for transforming narrative content into structured output that defines where individual information resides within the output may include the steps of receiving narrative content; scanning the narrative content using a natural language processing (NLP) engine to identify a section and at least one clinical assertion within that section; extracting information from the narrative content, wherein the extracted information includes the section, the clinical assertion, and a plurality of elements, wherein the elements may include section elements and clinical assertion elements that annotate the section and clinical assertions respectively; identifying the section elements of the section and assigning a label to at least one section element based on a clinical model; identifying the clinical assertion elements of the clinical assertion and assigning a label to at least one clinical assertion element based on the clinical model; and organizing the section, clinical assertion, section elements, and clinical assertion elements within a schema.

In some embodiments, the labels are defined by a clinical model. In some embodiments, the labels assigned to the clinical assertion elements are selected from a predetermined list, wherein the list is predetermined based on a clinical assertion type. In some embodiments, the clinical model is represented as labels within the output schema. In some embodiments, the method may further include the step of integrating the structured output with at least one of an application component, application infrastructure, application, and end-user application. In some embodiments, the method may further include the step of powering an analytics system, EHR, data warehouse, or other application with the structured output. In some embodiments, the method may further include the step of storing or using the information within an electronic health record, data warehouse, health information exchange, or other application able to store structured output. In some embodiments, the method may further include the step of providing processed unstructured data to an application for one of analytics, compliance, regulatory compliance, quality improvement, cost reduction, and any other suitable application that utilizes healthcare data.

In some embodiments, the section is a heading within the narrative note that suggests context for subsequent text. In some embodiments, the subsequent text includes at least one clinical assertion. In some embodiments, the clinical assertion describes clinical information related to a patient. In some embodiments, a label assigned to the section element may describe at least one of title, text, code, and other suitable concept.

In some embodiments, the method may further include the step of identifying secondary section elements that appear zero to many times for a given section depending on the section elements. In some embodiments, the method may further include the step of assigning a secondary label to at least one secondary section element, wherein a list of secondary labels may include section name, sentence, id, phrase, code value, code system, code system name, display name, and any combination thereof. In some embodiments, a clinical assertion is referenced as an element within a section.

In some embodiments, the labels that further characterize clinical assertion elements are data elements that modify, annotate or qualify the clinical assertion and are herein referenced as properties. In some embodiments, the properties are identified from a subset of properties, wherein the subset of properties is determined based on the clinical assertion type. In some embodiments, the subset of properties includes groups of related properties. In some embodiments, the property groups assigned to a clinical assertion are determined by the clinical assertion type. In some embodiments, the clinical assertion type is at least one of several concepts, including allergy, demographic, device, immunization, lab, medication, problem, procedure, physiologic, or concepts clinically similar to these terms. In general, methods described herein for transforming narrative content into structured output that defines where individual information resides within the output may include the steps of receiving narrative content; scanning the narrative content using a natural language processing (NLP) engine to identify at least one section, at least one clinical assertion within that section, and at least one element that annotates at least one of the section and the clinical assertion; extracting information from the narrative content including the section, the clinical assertion, and the element; describing at least one element with a label selected from a predetermined list of labels within a clinical model, wherein the predetermined list of labels differs according to a type of information to be described; and organizing the section, clinical assertion, and elements, within an extensible markup language (XML) schema.

In some embodiments, the method further includes the step of integrating the structured output with at least one of an application component, infrastructure application, application, and end-user application. In some embodiments, the method further includes the step of providing an analytics system, EHR, data warehouse, or other application with the structured output.

In some embodiments, the section is a heading within the narrative note that suggests context for subsequent text. In some embodiments, the subsequent text includes at least one clinical assertion. In some embodiments, the clinical assertion is an assertion within the narrative note that describes clinical information related to a patient. In some embodiments, the method further includes the step of identifying at least one secondary element that modifies the element. In some embodiments, the predetermined list of labels within the clinical model differs according to a clinical assertion type of the clinical assertion. In some embodiments, the label that describes an element that modifies the clinical assertion is defined as a property. In some embodiments, the clinical assertion type is at least one of several concepts, including allergy, demographic, device, lab, medication, problem, procedure, physiologic, or concepts clinically similar to these terms.

In general, methods described herein for transforming narrative content into structured output that defines where individual information resides within the output include the steps of receiving narrative content; scanning the narrative content using a natural language processing (NLP) engine to identify a clinical assertion; parsing the clinical assertion into individual components; and using a clinical model to annotate the individual components within the clinical assertion by describing at least one of the individual components with a label selected from a predetermined list of labels within the clinical model.

In some embodiments, the predetermined list of labels differs according to a type of information to be described. In some embodiments, the method further includes the step of mapping a whole or part of the labeled individual components to codes within at least one terminology standard. In some embodiments, the method further includes the step of passing the labeled individual components (postcoordinated terms) to a terminology engine. For example, the terminology engine may be software that maps a term to a controlled vocabulary (precoordinated terms). In some embodiments, the terminology engine may reside within the NLP engine. In some embodiments, the terminology engine may be external to the NLP engine. In some embodiments, the terminology engine may be provided by a terminology service provider.

In some embodiments, the method further includes the step of utilizing an algorithm to match a clinically important set of properties within a clinical assertion (postcoordinated terms) to at least one code within a terminology (precoordinated terms). In some embodiments, the algorithm uses labels within a clinical model to determine which properties are most important for a given clinical assertion type. In some embodiments, the algorithm uses permutations of postcoordinated terms of a clinical assertion, first attempting to find a match based on the most important elements based on the clinical model, and subsequently removing the least important elements based on the clinical model, until a coding match is found for the most important subset or permutation of elements within a clinical assertion to a given terminology.

In some embodiments, the parsing the clinical assertion step further comprises parsing the clinical assertion into postcoordinated terms, which are discrete terms that modify or qualify a clinical assertion. In some embodiments, the parsing the clinical assertion step further comprises extracting the clinical assertion from the narrative content. In some embodiments, the clinical model comprises a plurality of labels that may be assigned to the clinical assertion and its individual components. In some embodiments, all clinical assertions and individual components are annotated with a label from the clinical model.

In general, methods described herein for transforming narrative content into structured output, may include the steps of: receiving narrative content; scanning the narrative content using a natural language processing (NLP) engine to identify a clinical assertion; parsing the clinical assertion into individual components; and describing at least one of the individual components with a label selected from a predetermined list of labels within a clinical model, wherein the predetermined list of labels differs according to a type of information to be described; and providing the annotated components to a terminology engine for mapping to a lexicon or ontology.

In some embodiments, the providing step further comprises providing postcoordinated content to be mapped to corresponding codes, wherein the postcoordinated content comprises a set of elements prioritized based on the clinical assertion type and clinical model labels.

In some embodiments, the postcoordinated content supports aggregation of data elements and subsequent data mining. In some embodiments, the providing step further comprises providing the postcoodinated content to be mapped to precoordinated content, which are codes related to the clinical assertion. In some embodiments, the precoordinated content supports data mining. In some embodiments, further comprising the step of utilizing the postcoordinated content and the precoordinated content to support subsequent data mining.

In some embodiments, the mapping step is performed by a terminology engine, software that maps a term to a controlled vocabulary. In some embodiments, the corresponding codes align with a lexicon. In some embodiments, the lexicon may include at least one of ICD-9, ICD-10, LOINC, CPT, and RxNorm. In some embodiments, the corresponding codes align with a language that incorporates associations between terms. In some embodiments, the corresponding codes align with an ontology. In some embodiments, the corresponding codes align with SNOMED.

In general, the methods described herein for transforming narrative content into structured output, may include the steps of receiving narrative content; scanning the narrative content using a natural language processing (NLP) engine to transform the data set into a plurality of concepts within a plurality of distinct contexts; parsing at least one concept into individual elements; annotating at least one of the individual elements with labels within a clinical model; prioritizing a set of the individual elements based on a predetermined priority list, wherein the predetermined priority list differs according to a concept type; and deriving codes based on a prioritized permutation of the individual elements, wherein the prioritized permutation of the individual elements is the highest priority permutation that is recognized within a given coding system. In some embodiments, the codes are derived from a terminology engine.

In some embodiments, the annotating step comprises transforming the individual elements into postcoordinated content. In some embodiments, the annotating step comprises describing at least one of the individual elements with a label selected from a predetermined list of labels within the clinical model, wherein the predetermined list of labels differs according to a concept type.

In general, the systems described herein for processing patient information may include a natural language processing (NLP) engine configured to receive a data set and to transform the data set into a plurality of concepts within a plurality of distinct contexts; and a clinical model configured to structure the plurality of concepts by annotating concepts and creating aggregations of the concepts.

In some embodiments, the NLP engine and clinical model output are ordered within a schema to support integration within an external data mining engine. In some embodiments, the NLP engine and clinical model represent a data extraction system. In some embodiments, the data extraction system is integrated with at least one of a data storage solution, data mining engine, interoperability solution, and electronic health record.

In some embodiments, the plurality of distinct contexts are medical contexts. In some embodiments, the data set includes at least one encounter note. In some embodiments, the encounter note was typed, written, dictated, or otherwise captured from a physician, nurse, or other healthcare provider. In some embodiments, the NLP engine is configured to scan the data set and to use concepts in the data set to transform the data set into a plurality of concepts within a plurality of distinct contexts.

In some embodiments, a clinical model based output from the system, representing postcoordinated output, supports aggregation of data elements and subsequent data mining. In some embodiments, the system may further include an ontology or lexicon configured to structure the plurality of concepts by annotating relationships between the concepts and creating aggregations of the concepts with coded output. In some embodiments, the system is further configured to provide coded annotation, representing precoordinated output, wherein the precoordinated output supports a subset of data storage, data mining, and interoperability. In some embodiments, the postcoordinated and precoordinated output are configured to be used together to support a subset of data capture, data storage, data transformation, and data mining of information.

In some embodiments, the system may further include an integration engine that functions to pass postcoordinated content from the system to an external application. In some embodiments, the integration engine functions to pass the postcoordinated content to an application that maps the postcoordinated content to corresponding precoordinated codes. In some embodiments, the integration engine functions to pass the postcoordinated content to a terminology engine for postcoordinated mapping.

In some embodiments, the integration engine prioritizes postcoordinated content to be mapped based on the clinical model. In some embodiments, the clinical assertion element labels, referencing the clinical model, determine which postcoordinated elements are most important for coding. In some embodiments, the providing step includes providing a set of clinical assertion elements for mapping to a specific terminology or ontology, where if mapping is not possible based on limitations of the terminology engine or lexicon or ontology, a different permutation of elements is provided for coding based on the relative importance of the properties within the clinical model for a given clinical assertion type.

In general, methods for transforming narrative content into structured output may include the steps of receiving narrative content; scanning the narrative content using a natural language processing (NLP) engine to identify a term within the narrative content; determining that the term identified by the NLP engine is unknown to the NLP engine; providing the unknown term to a terminology engine; receiving an output from the terminology engine; and training the NLP engine with the terminology engine to define the term.

In some embodiments, the steps of providing the unknown term, receiving an output from the terminology engine, and training the NLP engine are automated. In some embodiments, the steps of providing the unknown term, receiving an output from the terminology engine, and training the NLP engine are supervised by a user. In some embodiments, the steps of providing the unknown term, receiving an output from the terminology engine, and training the NLP engine are performed by a user.

In general, a method for transforming narrative content into structured output that defines where individual information resides within the output may include the steps of receiving narrative content; scanning the narrative content using a natural language processing (NLP) engine to identify a clinical assertion; parsing the clinical assertion into individual components; using a clinical model to annotate the individual components within the clinical assertion by describing at least one of the individual components with a label selected from a predetermined list of labels within the clinical model; describing the clinical model within an XML schema; and describing the clinical assertion within an XML output as a clinical assertion annotated by data elements such as data elements and clinical model labels. In some embodiments, clinical labels within a schema may be utilized to define postcoordinated annotation.

In general, a method for A method for transforming narrative content into structured output may include the steps of receiving narrative content; scanning the narrative content using a natural language processing (NLP) engine to identify a clinical assertion; parsing the clinical assertion into individual components; and describing at least one of the individual components with a label within a clinical model, wherein the label emphasizes context for a clinical assertion. In some embodiments, the label indicates that the individual component described by the label influences retrieval and usage by a subsequent application. In some embodiments, the label comprises a special name or characteristic to suggest that the individual component described by the label influences retrieval and usage by a subsequent application. In some embodiments, the label indicates that the clinical assertion is historical rather than current. In some embodiments, the label indicates that the clinical assertion was not experienced by the subject of the narrative content. In some embodiments, the label indicates that the clinical assertion is not definitive. In some embodiments, the label indicates that the individual component described by the label influences retrieval and usage by a subsequent user. In some embodiments, the label indicates that the individual component described by the label influences retrieval and usage by a software development kit.

DETAILED DESCRIPTION

Figure 1:
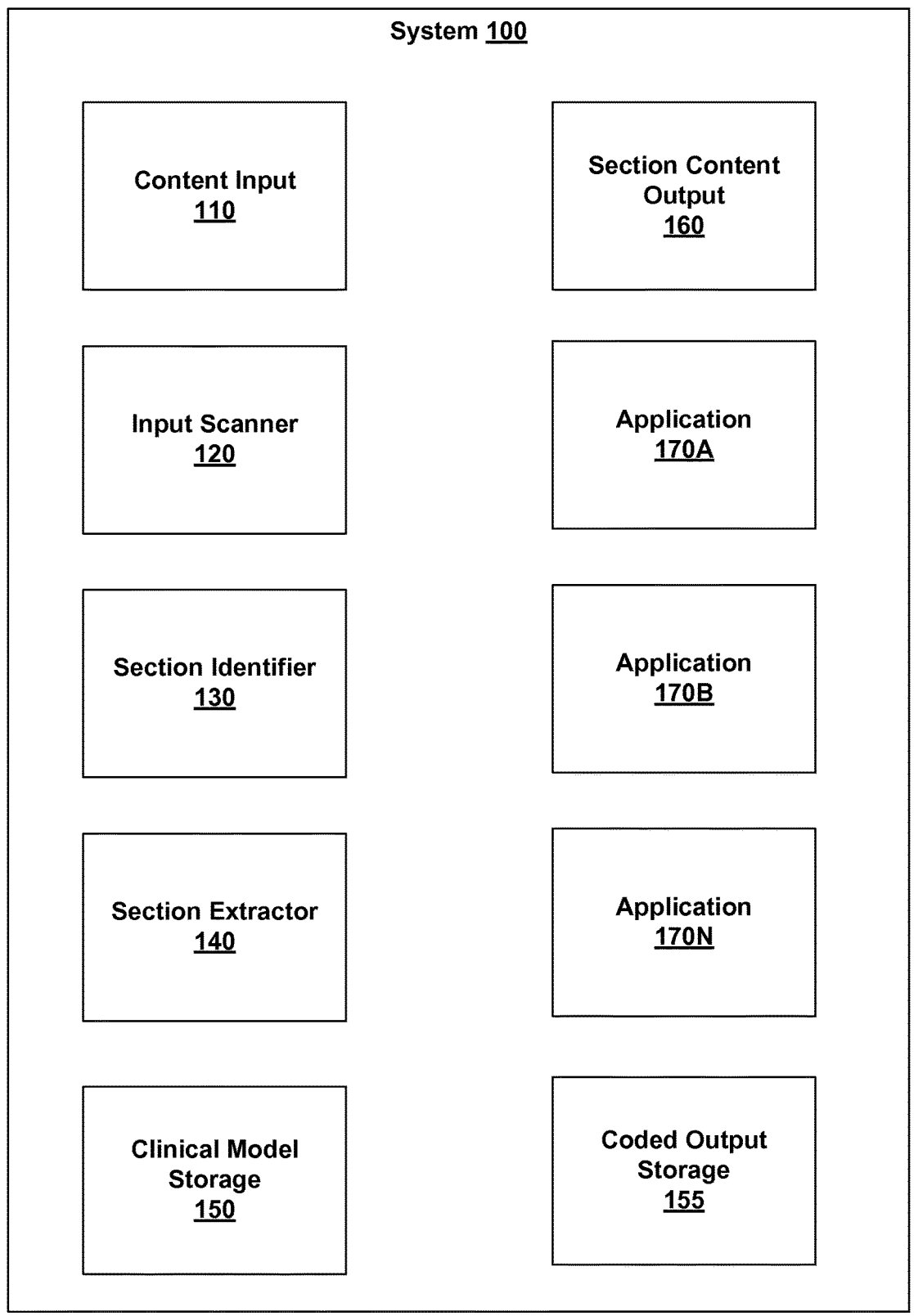
FIG. 1 illustrates a system for transforming narrative content into structured output, according to various embodiments.

Described herein are systems and methods for processing data. In some embodiments, the systems and methods described herein may be utilized with electronic health records (EHRs), data warehouses, analytics applications, and other applications within healthcare. In some embodiments, the systems and methods described herein may be for transforming narrative content into structured output that defines where individual information resides within the output. In some embodiments, the systems and methods described herein may be for transforming narrative content into structured output for subsequent application-based use.

Healthcare applications are only as good as the data that drives them. Information in healthcare is all around us and comes in many different forms. However, the majority of applications in the market today cannot access the data they need. Current methods of data extraction are primarily manual, making them slow, expensive and often ineffective. In modern EHR systems only 20% of data are structured, or machine readable for downstream applications. The other 80% of healthcare data are unstructured and unusable for downstream applications without data extraction. The systems and methods described herein allow unstructured content to be meaningfully accessed and analyzed.

The information required by most healthcare applications is known. Whether related to quality measures, revenue capture, EHR, or other applications in the provider, payer, pharmaceutical or other markets, broad needs exist. Attempting to meet these needs with claims or administrative data or with the discrete data captured within an EHR has proven difficult and, at times, impossible. To address this challenge, an ever growing army of coders has been hired to manually extract information for a subset of patients for specific use cases. Whether the goal is recognition of a quality measure such as smoking, poorly controlled diabetes, or ventilator associated pneumonia, or the goal is specific to a given market or need, information is being extracted from electronic and paper patient charts on a manual basis every day for almost every patient encounter. The extraction process normalizes and codes the data, supporting utility for downsteam machine-based applications. Use of healthcare data by applications underpins the majority of forward-looking efforts to create systems to improve care and reduce costs.

Information is most commonly manually extracted from the richest source of patient data, clinical narrative notes. A patient narrative note is created for almost every patient encounter, by every provider, every day. Patient narratives are critical to the practice of healthcare and accomplish at least two goals that checkboxes and dropdowns do not. They contain detailed information on the patient that forms the primary source of historical information used by the physician in subsequent encounters. They also form the foundation of the legal record, used to support billing and to review in cases of potential errors in management. Patient narrative notes represent the majority of the 80% of healthcare information that is considered unstructured and thus unusable for downstream applications. If this information could be automatically extracted in a systematic way that would support downstream data usage, the effects in the healthcare system could be powerful. A massive amount of needed information could be liberated in an accurate, rapid, and robust way for use to improve healthcare quality and reduce costs.

The systems and methods described herein structure data in new and unique ways. In some embodiments, the systems and methods described herein automate the usage of narrative notes for analytics. In some embodiments, the systems and methods described herein automate the usage of narrative notes for quality improvement. In some embodiments, the systems and methods described herein automate the usage of narrative notes for compliance. In some embodiments, the systems and methods described herein automate the usage of narrative notes for cost reduction. In some embodiments, the systems and methods described herein automate the usage of narrative notes for revenue cycle management. In some embodiments, the systems and methods described herein automate the conventional manual coding performed by a provider or coder, resulting in easier and more effective documentation (e.g. charting). In some embodiments, the systems and methods described herein automate data storage, which may include data transformation and may include transformation for interoperability. In some embodiments, the systems and methods described herein automate workflow in healthcare related to revenue cycle management, interoperability, electronic health records, and other systemic needs.

In some embodiments, the systems and methods described herein perform an automated extraction of data from original documents including unstructured clinical text. In some embodiments, these data are extracted while annotating along a clinical model. In some embodiments, these data are extracted while coding to a lexicon, such as ICD-9. In some embodiments, these data are extracted while coding to an ontology, such as SNOMED. This automated data extraction may be faster, more comprehensive, and more efficient than manual data extraction, saving time and money. The systems and methods described herein may be coupled to or partnered with applications built on top of a robust data layer which incorporates processed unstructured data. In some embodiments, the data are extracted and organized into a highly annotated document that may be stored, potentially for later use. In some embodiments, the data are extracted and organized into a highly annotated document that may be used by applications, such as analytics, compliance, transcription, revenue cycle management, EHR, and other applications that can use healthcare data. The extracted data may provide a robust data layer able to empower applications. In some embodiments, applications may include healthcare applications to address quality, billing, clinical research, and challenges inherent in meaningful use, accountable care organization, and ICD-10 conversion. The extracted data may also provide further insight into previously unusable unstructured content.

In some embodiments, the data are extracted and organized into a highly annotated document that may be integrated directly with applications, such as a data warehouse, an analytics application, EHR, interoperability application, revenue cycle management application, or other healthcare software application or service. In some embodiments, the data may be provided to multiple applications. In some embodiments, the highly annotated output may be used within at least one of the provider, payer, and pharmaceutical industry.

In some embodiments, the source data may be formatted within an output schema designed to facilitate rapid understanding and integration of rich natural language processing content into an associated application. In some embodiments, the schema may combine a comprehensive and massively annotated representation of a narrative note coupled with a clinical model to define exactly how annotated information will be described. In some embodiments, assertions broken into component parts annotated by a clinical model (postcoordinated) supports further downstream use of data. In some embodiments, the clinical model annotated content is transformed into accurate and granular codes (precoordinated) by leveraging the individual data elements and information contained in the clinical model annotations. These methods and systems are described in detail below.

Definitions

As described herein, a "section" may be defined as a heading within a narrative note that suggests the context for subsequent text. In some specific embodiments, the sections may include Past Medical History, Allergies, Chief Complaint, Medications, Subjective, Objective, Assessment, Plan, Procedure, Description of Procedure, and a multitude of other section headings, including concepts using different text but clinically similar to these terms. In some embodiments, sections may represent a high level organization of the schema. In some embodiments, sections may represent a high level organization of the clinical model.

As described herein, a "clinical assertion" may be defined as an assertion within the narrative note that describes clinical information related to a patient. Clinical assertions may include any suitable clinically meaningful information regarding the patient or an aspect of the patient and may describe a broad array of information. A clinical assertion may also be known as a clinical statement, clinical knowledge, and a clinical concept. A clinical assertion type may be defined as the type of assertion that the clinical assertion is making in regards to the patient or an aspect of the patient which relates to healthcare. As an example, the clinical assertion of "hypertension" might be considered a problem (the type of clinical assertion,) while "atenolol" might be considered a medication (the type of clinical assertion). Elements may be defined as individual components that make up the concepts within a narrative note, specifically the individual components of the sections and clinical assertions, for example. More specifically, elements may modify or qualify the sections and clinical assertions. Elements may include any additional information related to a specific section, clinical assertion, or other elements. As such, section elements may be defined as elements that modify or qualify the sections of a clinical note, and clinical assertion elements may be defined as elements that modify or qualify the clinical assertions of a clinical note. Properties may be defined as the labels (within a clinical model) that describe clinical assertion elements. Properties may be used to modify or qualify clinical assertions and, thus, function as clinical assertion elements. A property group may be defined as a group or list of related properties.

"Postcoordinated content" may be defined as content including a set of elements that make up a given clinical assertion. "Postcoordinated output" may also be known as postcoordinated terms, postcoordinated content, individual components, and atomic representation of a concept. Precoordinated content may be defined as content including coded values related to the clinical assertion. Precoordinated content may also be known as codes, coded content, and precoordinated terms. An "ontology" may be defined as a rigorous and exhaustive organization of a knowledge domain that is usually hierarchical and contains relevant entities and their relations. An ontology may be a formal representation of the knowledge by a set of concepts within a domain and relationships between those concepts. It may be used to reason about the properties of that domain. An example of an ontology is SNOMED. A "lexicon" may be defined as a formal representation of language. A lexicon may be distinguished from an ontology in that an ontology contains associations between terms. Examples of lexicons include International Classification of Diseases (ICD), ICD-9, ICD-10, "Current Procedural Terminology" (CPT), CPT-4, Logical Observation Identifiers Names and Codes (LOINC), and RxNorm. Terminology is a system of terms belonging or peculiar to a science, art, or specialized subject. Examples of terminologies include ontologies and lexicons.

"Structured content" may refer to several forms of structure, including at least one of encoding, annotating, and ordering. "Narrative content" is information related to a patient encounter that is written in medical language. An example is "Patient X is a 57 year old man who presents complaining of right leg pain." Narrative content may also be known as narrative note, patient note, clinical note, encounter note, unstructured data, or a combination thereof. Structured content may also be known as structured output, structured note, and structured data.

"Modifying" a clinical assertion may be known as changing the meaning. For instance, adding the term "no" to "cancer" would change the meaning from "cancer" to "no cancer". "Qualifying" a clinical assertion may be known as adding to the meaning. For instance, adding the term "type 2" to "diabetes" would clarify the meaning from "diabetes" to "type 2 diabetes". XML is extensible markup language. An "element" may be a structured data element. Elements may qualify or modify other elements. For example, a problem clinical assertion may have elements "diabetes" and "250.00", each of which provides further information related to that clinical assertion. A "property" may be defined as an element that qualifies or modifies a clinical assertion. For example, diabetes may be labeled as a primary term for a problem clinical statement and 250.00 may be labeled as an ICD-9 code for the same problem clinical statement. The labels "primaryTerm" and "ICD-9" may be the properties and "diabetes" and "250.00" may be the property values. In general, a "label" conveys meaning and the specific term used for the label may be substituted with a different term with similar meaning. For example, diabetes may be labeled with primaryTerm or with another concept that conveys similar meaning in this context, such as problem, disease, disorder, or a custom term designed to convey clinical meaning attached to that clinical assertion element. An "annotation" may be a data element that adds content or context to another data element. For example an element may annotate another data element by qualifying or modifying it, or a label may be used to annotate or further describe a data element. A "label" may be an item within a clinical model used to offer further content or context to a data element. For example, hypertension may be labeled as the primary term for a problem or Tylenol may be labeled as the primary term for a medication. The clinical statement for hypertension may be labeled a problem. A label may represent a specialized annotation used within a schematic representation of knowledge.

These definitions of terms listed here, and throughout this specification, are for clarification purposes only and are not intended to limit the scope of these terms.

Systems for Processing Patient Information

In general, the systems described herein for processing patient information may include a natural language processing (NLP) engine configured to receive a data set and to transform the data set into a plurality of concepts within a plurality of distinct contexts; and a clinical model configured to structure the plurality of concepts by annotating concepts and creating aggregations of the concepts. In some embodiments, the NLP engine and clinical model output are ordered within a schema to support integration with a data mining engine. In some embodiments, the NLP engine and clinical model represent a data extraction system. In some embodiments, the data extraction system is distinct from downstream applications.

In some embodiments, the data set includes at least one encounter note. The encounter note may be, for example, a History and Physical (H&P) note, a Subjective, Objective, Assessment, and Plan (SOAP) note, a radiology note, a pathology note, a procedure note, or another note type. In some embodiments, the plurality of distinct contexts are medical contexts. The medical contexts may include, for example, history of present illness, past medical history, past surgical history, allergies to medications, current medications, relevant family history, and social history, other contexts, or concepts clinically similar to these terms. In some embodiments, the contexts may be considered sections. In some embodiments, the concepts may be clinical assertions, or clinical statements such as "acute bleeding duodenal ulcer" or "severe worsening nausea".

Natural Language Processing (NLP) Engine

In some embodiments, the natural language processing (NLP) engine is configured to receive a data set and to transform the data set into a plurality of concepts, or clinical assertions, within a plurality of distinct contexts, or sections. In some embodiments, the concepts are noun phrases recognizable by the NLP engine. In some embodiments, other grammatical phrases provide additional information to the NLP engine. In some embodiments, the NLP engine is configured to scan the data set and to use concepts in the data set to transform the data set into a plurality of concepts within a plurality of distinct contexts. Alternatively, in some embodiments, the NLP engine is configured to employ an algorithm to scan the data set and to apply syntactic and semantic rules to the data set to transform the data set into a plurality of concepts within a plurality of distinct contexts.

In some embodiments, the NLP engine, in conjunction with a clinical model, may transform the data set into machine-interpretable structured data by associating tags, or labels, to specific concepts—for instance labeling the word "hypertension" with a label indicating that "hypertension" is a primary term (for example, the label "primaryTerm", or any other similar label) within a problem clinical assertion type (for example, with the label "problem", or any other clinically similar term) within a past medical history section. In some embodiments, the concepts and/or individual components of the concepts, may be described with a label selected from a predetermined list of labels, or properties, within a clinical model. In some embodiments, the predetermined list of labels may differ according to a type of information to be described, for example the type of clinical assertion or concept. In some embodiments, the label is represented as an annotation. In some embodiments, the label is represented as an XML element or attribute.

In some embodiments, the NLP engine may employ algorithms to scan unstructured text, apply syntactic and semantic rules to extract computer-understandable information, and create a targeted, standardized representation. Alternatively, the NLP engine may scan the text for concepts (e.g. hypertension) and associate a tag with the word (e.g. "past medical history"). For example, the NLP engine may be configured to scan the text to identify concepts in the text.

In some embodiments, the NLP engine may recognize semantic metadata (concepts, at least one of modifiers and qualifiers, and the relationships between them) in the data set and map the semantic metadata to a relevant coded medical vocabulary. This may allow data to be used in any system where coded data are required. This may include reasoning-based clinical decision support systems, computer-assisted billing and medical claims, automated reporting for meaningful use, quality, analytics, quality improvement, efficiency improvement, and other applications.

In some embodiments, the NLP engine may perform pre-processing functions. Those functions may include any combination of spell-checking, document structure analysis, sentence splitting, tokenization, word sense disambiguation, part-of-speech tagging, and parsing. In some embodiments, contextual features including negation, temporality, and event subject identification may be utilized in an interpretation of the data set. In some embodiments, the NLP engine may include a combination of the following components: tokenizer, sentence boundary detector, part-of-speech tagger, morphological analyzer, shallow parser, deep parser, gazetteer, named entity recognizer, discourse module, template extractor, and template combiner.

The NLP engine may use one of several different methods (or a combination thereof) to extract information and transform the data set into a plurality of concepts within a plurality of distinct contexts. These methods may include methods such as pattern matching or more complete processing methods based on symbolic information and rules or based on statistical methods and machine learning. In some embodiments, as described herein, the information can be used for decision support and to enrich the data set within a system such as an electronic health record.

In some embodiments, pattern matching exploits basic patterns over a variety of structures—text strings, part-of-speech tags, semantic pairs, and dictionary entries. Alternatively the NLP engine may use shallow and full syntactic parsing. In some embodiments, as described in more detail below, a clinical model driven natural language processing system maps the concepts to a clinical model to guide the processing of the data set. Syntactic and semantic parsing approaches may combine the two in one processing step.

When extracting information from the data set, such as narrative text documents, the context of the concepts may be extracted. In some embodiments, this contextual information may include any combination of negation (e.g. "denies any abdominal pain"), temporality (e.g. " . . . appendectomy 2 years ago . . . "), and event subject identification (e.g. "his mother has diabetes"). In some embodiments, contextual features may include Validity (e.g valid/invalid), Certainty (e,g, high, moderate, low), Directionality (affirmed, negated, resolved), and Temporality (e.g. recent, during visit, historical). In some embodiments, contextual information or features may include qualifiers such as body location, laterality (e.g. left-handedness, right-footedness), direction (e.g. caudal, cephalad, etc.), or any other suitable qualifier. In some embodiments, contextual information or features may include modifiers such as negation, subject (e.g. patient or family member), temporality (e.g. a previous and not a current medication.), or any other suitable modifier. In some embodiments, these features that add information to the clinical assertion, may be explicitly defined within a clinical model with properties such as negation, subject, and certainty. In some embodiments, contextual information or features may include section. In some embodiments, the terms are annotated with the clinical model properties to provide additional context to the clinical assertion and clinical assertion elements. In some embodiments, the system may identify a large array of contextual features and metadata, which may be labeled in the form of annotations.

In some embodiments, the systems and methods may include a parser, which determines the structure of a sentence. For example, for each sentence, the system and method may generate a set of structured findings, such as problems (congestive heart failure), medications (beta blocker), or procedures (cervical screening) along with associated qualifiers, modifiers, or elements, such as certainty (no, high certainty), status (previous, new), body location (lung), section (Assessment), and other findings, or concepts clinically similar to these terms. In some embodiments, the parsed output is organized within sections, defining clinical context. In some embodiments, assertions are organized as clinical assertions within sections. In some embodiments, the structured findings are postcoordinated output, representing modifiers and qualifiers of a clinical assertion. In some embodiments, the postcoordinated output is annotated using a clinical model. For example, the phrase "History of present illness: A 57 year old man with poorly controlled type 2 diabetes mellitus" may be represented within the section "history of present illness", or other clinically similar section, and may contain a demographic type clinical assertion of "age 57" and gender type clinical assertion of "male" and another clinical assertion of "diabetes mellitus". The clinical assertion of "diabetes mellitus" may include qualifiers of "poorly controlled" and "type 2". "Poorly controlled" may be labeled as "status", "temporal status", or something clinically similar; and "type 2" may be labeled as "descriptive information" for example.

NLP Engine and Machine Learning

In some embodiments, the NLP engine may be utilized for machine learning. Machine learning may be defined as the process by which computers are directed to improve their performance over time or based on previous results.

In some embodiments, machine learning in natural language processing may occur based on user correction of system output. In some embodiments, user correction may be based directly on NLP engine output. In some embodiments, user correction may be within an application that uses data from the NLP engine output, either directly or subsequent to data transformation. In some embodiments, user correction automatically influences the system. In some embodiments, user correction influences the system only after manual review (supervised machine learning). In some embodiments, system improvement is specific to a given user or group of users. In some embodiments, system improvement is global.

In some embodiments, machine learning in natural language processing may occur based on direct or indirect feedback from the end user. For example, coded or otherwise annotated items corrected by a user or software within a transcription service, electronic health record, analytics platform, or other application, may be used to define errors or areas that can be improved within a natural language processing engine in an automated or supervised learning approach. Supervised learning may be defined as a process which provides feedback to a system wherein system improvement requires a manual intervention or offers the opportunity for a manual review.

In some embodiments, machine learning in natural language processing may occur based on integration with a terminology engine. In some embodiments, the terminology engine may be software that maps a term to a controlled vocabulary. For example, an unknown term may be parsed based on syntax and related to the terminology engine. If the terminology engine understands the context or other information related to that term, the NLP engine may improve and/or may be directed to improve based on that automated or supervised transfer of knowledge.

Terminologies

In some embodiments, the system may further include at least one of an ontology and lexicon configured to structure the plurality of concepts by annotating relationships between the concepts and creating aggregations of the concepts. In some embodiments, coded output is included as an annotation. In some embodiments, multiple code sets are included as annotations. In some embodiments, multiple code sets are included as annotations with different code sets used based on the clinical assertion. In some embodiments, the system is further configured to provide coded annotation, representing precoordinated output, wherein the precoordinated output supports data mining. In some embodiments, a clinical model based output from the system, representing postcoordinated output, also supports aggregation of data elements and subsequent data mining. In some embodiments, the postcoordinated and precoordinated output are configured to be used together to support a subset of data capture, data storage, data transformation, and data mining of information.

Related to terminologies used, an ontology and/or lexicon may be configured to structure the plurality of concepts by annotating relationships between the concepts and creating aggregations of the concepts.

In some embodiments, a used ontology is the Systematized Nomenclature of Medicine (SNOMED). SNOMED is a systematically organized computer-processable collection of medical terminology covering most areas of clinical information such as diseases, findings, procedures, microorganisms, substances, etc. It allows a consistent way to index, store, retrieve, and aggregate clinical data across specialties and sites of care. Conventional systems may use only 4-5 codes, such as billing level, low granularity codes. These codes may be collected using traditional manual processes, which may map the data to ICD-9, for example, a billing lexicon. In the systems and methods described herein, SNOMED may provide a far more relevant and granular coding. For example, SNOMED may provide information related to quality metrics that does not exist within the ICD-9 lexicon. SNOMED may allow an additional and more robust representation of patient data and inform better and more relevant care. For example, an application may seek relationships between computerized tomography (CT) scan usage and patient outcomes. Querying ICD-9 annotations would not lead to the desired information since ICD-9 does not have a code to represent CT scan. Querying SNOMED annotations may be more effective since SNOMED contains multiple codes representing different types of CT scans. Similarly, in assessing outcomes, a more granular ontology may provide rich information and associations which a lexicon such as ICD-9 cannot.

In some embodiments, a used ontology may include terminologies, or controlled vocabularies (CVs). A CV provides a list of concepts and text descriptions of their meaning and a list of lexical terms corresponding to each concept. Concepts in a CV are often organized in a hierarchy. Thus, CVs provide a collection of terms that can structure the plurality of concepts by annotating relationships between the concepts and creating aggregations of the concepts. In some embodiments, the ontology may include information models (or data models). An information model provides an organizing structure to information pertaining to a domain of interest, such as microarray data, and describes how different parts of the information at hand, such as the experimental condition and sample description, relate to each other.

In some embodiments, an ontology can provide a single identifier (the class or term identifier) for describing each entity and can store alternative names for that entity through the appropriate metadata. The ontology can thus be used as a controlled vocabulary to describe biomedical entities in terms of their functions, disease involvement, etc, in a consistent way. In addition, in some embodiments, the ontology can be augmented with terminological knowledge such as synonymy, abbreviations and acronyms.

In some embodiments, a used ontology may represent the data set itself, to provide an explicit specification of the terms used to express the biomedical information, such as the historical patient information. An ontology may make explicit the relationships among data types in databases, enabling applications to deduce subsumption among classes.

In some embodiments, an ontology may provide lexicons to recognize named entities or concepts in text. Alternatively, ontologies may guide the NLP engine by providing knowledge models and templates for capturing facts from text. In some embodiments, an ontology may make inferences based on the knowledge the ontology contains as well as any additional contextual information or asserted facts.

Terminology Mapping

In some embodiments, the system may further include an integration engine that functions to pass postcoordinated content (elemental content) from the system to another application. In some embodiments, the integration engine functions to pass the postcoordinated content to an application that maps the postcoordinated content to corresponding precoordinated codes. In some embodiments, the integration engine functions to pass the postcoordinated content to a terminology engine for precoordinated mapping. In some embodiments, the terminology engine may be a software engine designed to map discrete terms to one or more terminologies. In some embodiments, the terminology engine is software that maps a term to a controlled vocabulary. In some embodiments, the terminology engine may be an independent software entity provided by an independent terminology services company.

In some embodiments, systems and methods described herein for transforming a narrative note into a highly annotated document may further include an integration engine that functions to connect the output from the systems and methods described herein to an application.

In some embodiments, the application may be a terminology engine. In some embodiments, the integration engine will identify a clinical assertion and determine which application might be appropriate based on the clinical assertion type. In some embodiments, the integration engine may further pass on a set or subset of property values from the clinical assertion to the application, and receive back codes appropriate to the clinical statement to be included in the output schema. In some embodiments, the codes may include a subset of values from the ICD-9, ICD-10, SNOMED, LOINC, CPT, RxNorm, IMO, and other suitable code systems.

As an example, the term bleeding duodenal ulcer may be parsed by the systems and methods described herein as problem primaryTerm:ulcer; bodyLocation:duodenal; descriptiveInformation:bleeding. This information would then be passed to the integration engine, which would decide that a problem type clinical assertion should be passed to an application for mapping. The process might provide clinicians a way to enter a diagnosis for a patient Problem List without altering the language they would normally use for that diagnosis. An example of one such product includes Problem IT (Intelligent Medical Objects, Inc., Northbrook, Ill.). In some embodiments, the integration engine may check against an internal list of which problem properties were appropriate to use for coding of a problem. In this case, primaryTerm, bodyLocation, and descriptiveInformation, are all appropriate for coding of a problem. Thus, the terms "ulcer", "duodenal", and "bleeding" would be passed to the application, such Problem IT. For problem, the codes returned from the application may include ICD-9, ICD-10, SNOMED, and IMO terms. These may be incorporated into the output representation of the clinical assertion. The codes may be incorporated within the annotated output of the system. The codes may be incorporated within an XML representation. The codes may be further described within the XML schema. The labels listed above in this specific example, such as "problem", "primaryTerm", "bodyLocation", and "descriptiveInformation", and "code", may be formatted or named in any other suitable fashion to represent these concepts and/or other clinically similar concepts.

Data Format

In some embodiments, a system for processing patient data may further include at least one post processing engine. In some embodiments, a post processing engine may be a terminology engine. In some embodiments, a post processing engine may be incorporated or be based on an extensible stylesheet language. In some embodiments, a post processing engine may account for at least one of specific linguistic variation, terminology needs, downstream application needs, and end user requirements. In some embodiments, a post processing engine may be specific to a given solution partner, healthcare organization, hospital, and/or provider.

In some embodiments, the post processing engine may convert output from a NLP engine to a specific data format. In some embodiments, the initial engine output is green CDA. In some embodiments, initial engine output is converted to one or several data formats to support downstream storage and/or usage. In some embodiments, the structured data output from the NLP engine may be formatted in one of a Clinical Document Architecture (CDA), a Continuity of Care Record (CCR), and a Continuity of Care Document (CCD) format. In one example, the NLP engine or post processor may output an output schema based on a data structure (e.g. CDA) specification. The output schema may be extended to accommodate additional (rich) information embedded to improve at least one of usability, accuracy, quality of data, and interoperability. The transform may include coded concepts to be in compliance with the given format (e.g. CDA).

In some embodiments, the systems and methods may also include an encoder, which determines appropriate codes for the parsed output based on a coding table or terminology engine. Once the output is generated, it may be used as a structured document, stored as a structured document, stored in a structured data warehouse, used immediately to power an application, or used subsequently to power an application.

Additional Components

In some embodiments, the system may further include an integration engine that functions to pass postcoordinated content and/or precoordinated content from the system to another application. In some embodiments, an application may use the system output to gain or store information related to clinical care. In some embodiments, the application is at least one of: a data warehouse, EHR, analytics application, compliance application, and a health information exchange. In some embodiments, an application may use the system output to provide insight to another application or to an end user. In some embodiments, the application addresses at least one of: analytics, compliance, revenue cycle management, meaningful use, accountable care, population based health, care coordination, transcription, research, comparative effectiveness, cohort identification, pharmaceuticals, medical devices, healthcare cost reduction, and healthcare quality improvement.

Methods for Transforming Narrative Content into Structured Output, Including Description of Clinical Model Usage.

As shown in FIG. 1, system 100 described herein includes a content input 110, an input scanner 120, a section identifier 130, a section extractor 140, a clinical model storage 150, a coded output storage 155 and a structured content output 160. The output of structured content output 160 is optionally provided to one or more applications 170 (individually identified as 170A, 170B . . . 170N). These elements each include hardware, firmware and/or software stored on a non-transient computer readable medium. They each also include logic configured to perform specific functions as described elsewhere herein. This logic is embodied in the elements and includes hardware modified by computing instructions such that the hardware is configured to perform the specific functions.

Figure 2:
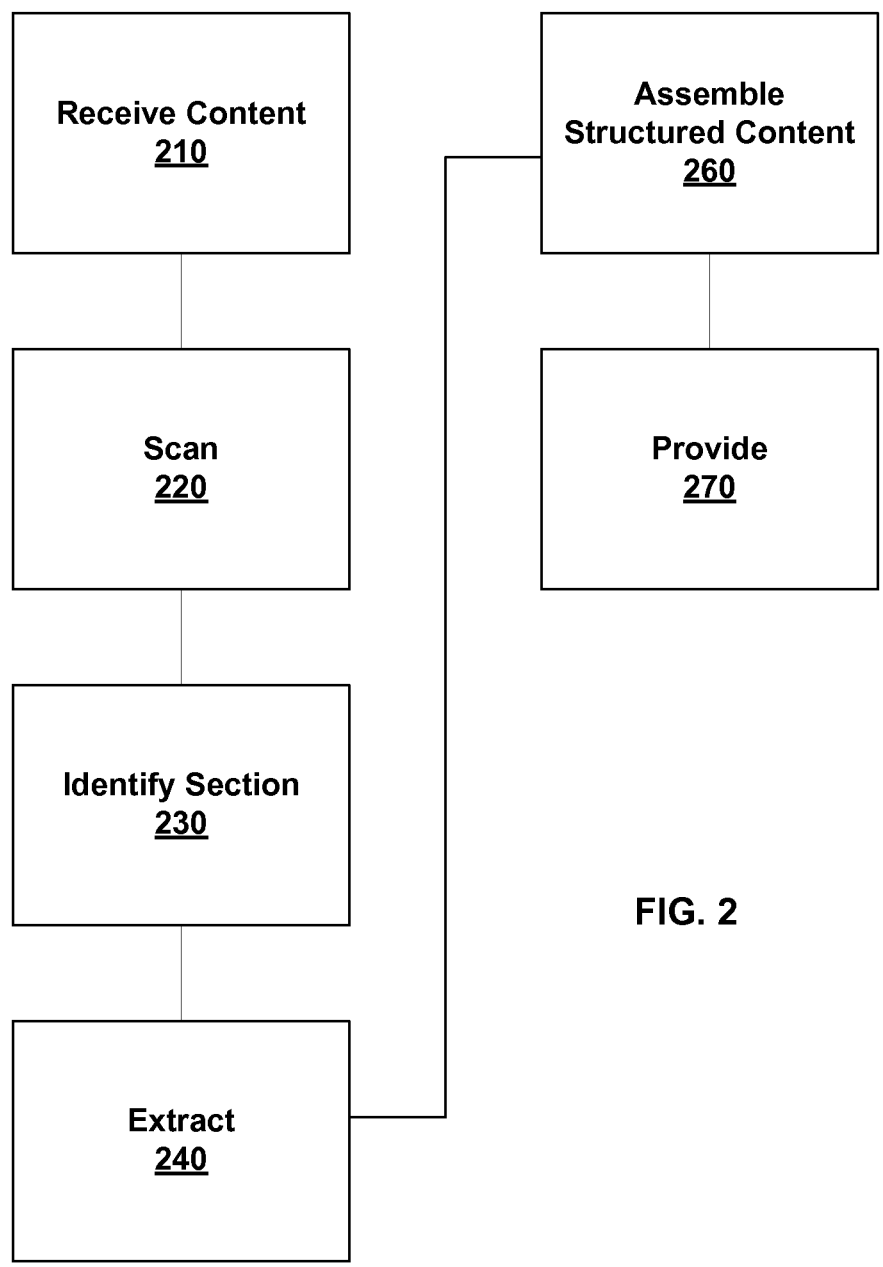
FIG. 2 illustrates method for transforming narrative content into structured output, according to various embodiments.

FIG. 2 illustrates a method of processing narrative clinical content, according to various embodiments of the invention. This method includes transforming narrative content into structured output that defines where individual information resides within the output may include the steps of receiving narrative clinical content. In a receive step 110 narrative clinical content is received at content input 110. The content is optionally received on a static memory, wirelessly, and/or via a computer network. In a Scan Step 220 the receive narrative content is scanned using input scanner 120. Input scanner 120 optionally includes a natural language processing (NLP) engine. In an identify section step 230 a section and at least one clinical assertion within that section is identified, optionally using section identifier 130. In an extract step 240 section extractor 140 is used to extract the section, the clinical assertion, and a plurality of elements, wherein the elements include section elements and clinical assertion elements that annotate the section and clinical assertions respectively. Extract step 240 is optionally performed using a clinical model stored in Clinical Model Storage 150. Identify section step 230 and extract step 240 optionally further include identifying the section elements of the section and assigning a label to at least one section element based on a clinical model; and identifying the clinical assertion elements of the clinical assertion and assigning a label to at least one clinical assertion element based on the clinical model. In an assemble structured content step 160 the structured content generated in identify section step 230 and extract step 240 is assembled into a schema. This schema can be in the form a database structure and/or can include metadata, or the like. The schema is made available to structured content output 160 and is optionally stored in coded output storage 155. Assemble structured content step 160 is optionally performed by section extractor 140. In an optional provide step 270 the structured content is provided to one or more of applications 170.

In some embodiments, labels are assigned to the clinical assertion elements in extract step 240. The labels are selected from a predetermined list, wherein the list is predetermined based on a clinical assertion type. This list may be stored in clinical model storage 150. In some embodiments, the method may further include the step of integrating the fully annotated structured content with one or more of several suitable applications. In some embodiments, the fully annotated structured content may be integrated with at least one of an application component, application, and end-user application. In some embodiments, Provide step 270 includes powering an analytics system, EHR, data warehouse, or other application with the structured output.

As shown in FIG. 2, methods described herein for transforming narrative content into structured output that defines where individual information resides within the output may include the steps of receiving narrative content using content input 110; scanning the narrative content using a natural language processing (NLP) engine of input scanner 120, identifying at least one section, at least one clinical assertion within that section, and at least one element that annotates at least one of the section and the clinical assertion, using section identifier 130; extracting information from the narrative content including the section, the clinical assertion, and the element, using section extractor 140; The result of this process is structured data describing at least one element with a label selected from a predetermined list of labels within a clinical model, wherein the predetermined list of labels differs according to a type of information to be described; and organizing the section, clinical assertion, and elements, within a schema, such as an XML schema. The resulting Data can be stored in Coded Output Storage 155 and communicated to applications using Section content output 160. These applications can include, for example, data warehouses, EMR, analytics applications, billing applications, and/or other applications.

Sections and Clinical Assertions

Figure 3:
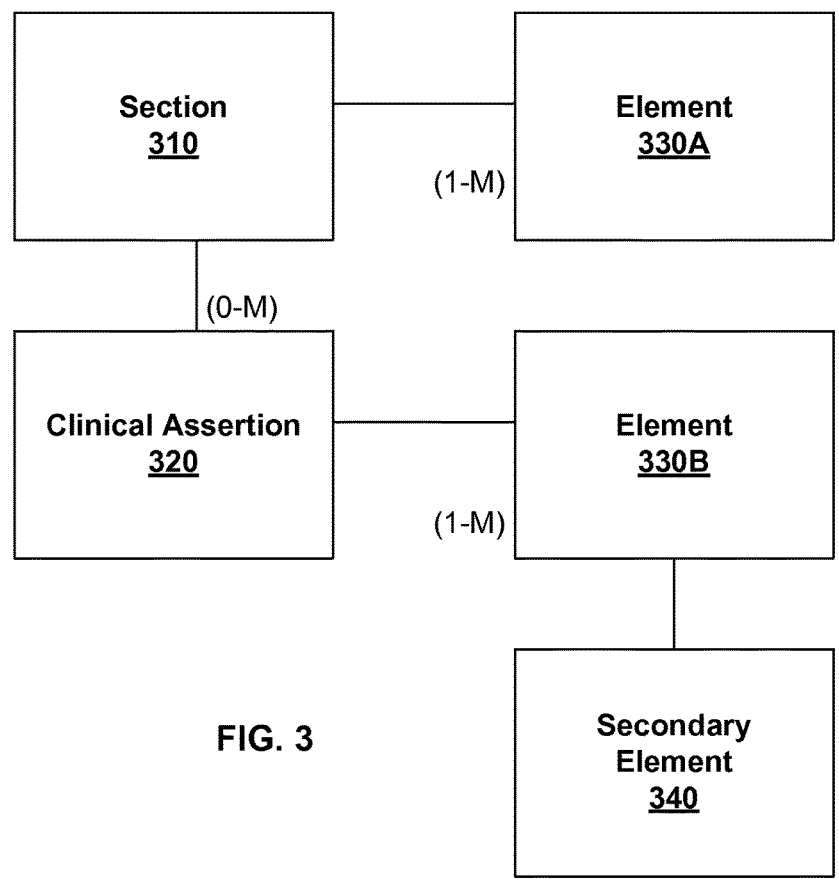
FIG. 3 illustrates one embodiment of objects within a schema, according to various embodiments.

In some embodiments, the narrative clinical content includes a narrative note, and the scan step 220 includes scanning the narrative note to identify a section and at least one clinical assertion within that section. In some embodiments, as described above, the step of scanning the narrative note may be performed using a natural language processing (NLP) engine of input scanner 120. In some embodiments, the clinical model, stored in clinical model storage 150, is organized around sections, clinical assertions and elements. A narrative note can be, for example, verbal notes dictated by a medical care giver. FIG. 3 illustrates objects within the output schema. The objects include at least one section 310 and have anywhere from one to many ([1-M]) elements 330 (A, B, etc) of the section (i.e. section elements). Further, as shown, the section may include zero to many ([0-M]) clinical assertions 320. As described above, the section 310 may suggest a context for the subsequent clinical assertion. Further, as shown, the clinical assertion 320 may include one to many ([1-M]) elements 330 of the clinical assertion (i.e. clinical assertion elements).

In some embodiments, the sections 310 are headings within the narrative note that suggest the context for subsequent text. In some specific embodiments, the sections 310 may include Past Medical History, Allergies, Chief Complaint, Medications, Subjective, Objective, other sections, and any other suitable section heading or concepts clinically similar to these terms. The narrative note often contains sections 310 that describe context, such as past medical history, history of present illness, medications, plan, subjective, objective, or a multitude of other aspects of care. Sections 310 may represent the top level organization of the clinical model. Each clinical assertion 320 may be described within a section 310. Consider the following example: Past medical history: diabetes, hypertension, and heart disease. Past surgical history: appendectomy and inguinal hernia repair". This exemplary note extract includes two sections 310: "past medical history" and "past surgical history". In this example, the first section 310, past medical history, contains three clinical assertions 320: diabetes, hypertension, and heart disease. The second section 310, past surgical history, contains two clinical assertions 320: appendectomy, inguinal hernia repair.

In some embodiments, the method may further include the step of identifying secondary section elements 340 of the section elements 330 and assigning a secondary label to at least one secondary section element 340. In some embodiments, the secondary label assigned to the secondary section element 340 describes at least one of several functions, including concepts such as section name, sentence, identification, phrase, code, code system, name of code system, or concepts similar to these terms. In one specific embodiment, the labels may be formatted as normalizedSectionName, sentence, id, phrase, codeValue, codeSystem, codeSystemName, and displayName or other suitable terms or terms with similar meaning.

In some embodiments, the clinical assertions 320 may be assertions within the narrative note that describe clinical information related to the patient. Broad information may be described within clinical assertions 320. There may be multiple types of clinical assertions 320. As an example, "hypertension" might be considered a problem type of clinical assertion 320, while "atenolol" might be considered a medication type of clinical assertion 320. A clinical assertion can potentially be qualified by a plurality of elements. A clinical assertion 320 can potentially be modified by a plurality of elements 330 and/or 340. For example, the clinical assertion "left heel ulcer" might be described as a problem clinical assertion having the following individual components, or elements 330: ulcer, left, and heel. In some embodiments, a plurality of the elements 330 may be labeled. In some embodiments, each of the elements 330 may be labeled. For example, ulcer may be labeled as the primary term (e.g. primaryTerm) of the clinical assertion. Further left may be labeled as the side of the body (e.g. bodySide) and heel may be labeled as the location of the body (e.g. bodyLocation). Further, there may be additional elements 330 such as an ICD-9 code and SNOMED code, and they would be labeled accordingly. Further examples of a clinical assertion 320 may include a clinical problem such as diabetes or a medication such as insulin.

Clinical assertions 320, sometimes described as clinical statements, within a narrative often represent an assertion regarding the patient or an aspect of the patient which relates to healthcare. Examples of clinical assertions 320 include demographic information (e.g. the patient is 57 years old), clinically critical information (e.g. current usage of atenolol for hypertension), or a detailed assertion (e.g. the patient has poorly controlled type 2 diabetes mellitus). Within a given clinical assertion 320, such as "poorly controlled type 2 diabetes", there are often elements 330, or individual components, such as "poor control", "type 2", and "diabetes mellitus", which provide clear representations of portions of the content within the clinical assertion 320. Clinical assertions 320 may come in multiple types. Examples include medical problem, medication, allergy, demographic, and many others. The clinical assertion 320 may be possible to represent by individual elements 330 (postcoordinated) such as "type 2", "diabetes mellitus", and "poor control" describing a single clinical concept. The clinical assertion 320 may be possible to represent by a code or codes (precoordinated), such as the ICD-9, ICD-10, or SNOMED code for type 2 diabetes mellitus. To empower a wide array of data uses in healthcare, there is a need for systems and methods to output clear representations of unstructured narrative data within a modeled, schema-driven, approach.

Elements

Information related to a specific section 310, clinical assertion 320, or other elements 330. As such, there may be section elements 330 of the sections 310 of a narrative note, and there may be clinical assertion elements 330 of the clinical assertions 320 of a narrative note. For example, a section element 330 may be a LOINC code. A clinical assertion 320 such as diabetes may have a clinical assertion element 330 of severity. In some embodiments, an element 330 may qualify or modify another element 330. For example, the clinical assertion diabetes may have an element 330 labeled code. The element code may be modified by elements 340 such as the type of code (e.g. ICD-9) and the value of the code (e.g. 250.00).

As an example, the phrase "Past surgical history: appendectomy and inguinal hernia repair" contains a section (past surgical history, in this example) with multiple clinical assertions (appendectomy and inguinal hernia repair, for example). A clinical statement such as "inguinal hernia repair" may be further broken up into postcoordinated concepts. The clinical assertion type for inguinal hernia repair may be "procedure". The clinical assertion type procedure may have a predetermined set of property groups within the clinical model that can qualify or modify procedure type clinical assertions 320, including body location properties, association properties, and others. In a specific example the postcoordinated output may be "procedure: primaryTerm: hernia repair, bodyLocation: inguinal, associated problem: inguinal hernia". The label "primaryTerm" may be formatted or named in any other suitable fashion to represent the concept of primary term or a clinically similar concept. The label "bodyLocation" may be formatted or named in any other suitable fashion to represent the concept of location on/in the body or a clinically similar concept. The label "associated problem" may be formatted or named in any other suitable fashion to represent the concept of an associated condition or a clinically similar concept. The precoordinated output may include a SNOMED code and a Current Procedural Terminology (CPT) code. The precoordinated output may include one or more codes from one or more terminologies.

Properties and Property Groups within a Clinical Model

In some embodiments, as shown in FIG. 2, the information extracted from the note may include the section 310, the at least one clinical assertion 320, and a plurality of elements 330 and/or 340. In some embodiments, the elements 330 and/or 340 include section elements and clinical assertion elements that qualify or modify the section 310 and at least one clinical assertion 320, respectively. In some embodiments, the method may further include the step of identifying the section elements 330A of the extracted section and identifying the clinical assertion elements 330B of the extracted clinical assertion. Further, a label may be assigned to each element 330. In some embodiments, the labels assigned to the clinical assertion elements 330B are selected from a predetermined list within a clinical model. The list may be predetermined based on the type of clinical assertion 320 extracted. These fully annotated data constrained by the schema, may then be outputted to support easy retrieval of information or integration with applications, such as a data warehouse, an analytics application, EHR, interoperability application, or other healthcare software application or service.

In some embodiments, the labels assigned to clinical assertions elements 330B may be called properties. In the example above, the clinical assertion "left heel ulcer" would be described as a medical condition (e.g. problem) type of clinical assertion 330 having the following elements 330: ulcer, left, and heel. In some embodiments, each of the elements 330 or individual components may be labeled. For example, ulcer may be labeled as the primary term (e.g. primaryTerm) of the clinical assertion. Further left may be labeled as the side of the body (e.g. bodySide) and heel may be labeled as the location on/in the body (e.g. bodyLocation). In this example, the elements left (side of the body, e.g. bodySide) and heel (location on/in the body, e.g. bodyLocation) directly qualify the clinical assertion left heel ulcer, and therefore these labels would be considered properties and the elements 330 "left", "heel" and "ulcer" would be considered property values. The labels "bodySide" and "bodyLocation" in this specific example may be formatted or named in any other suitable fashion to represent the concepts of directionality, location, and/or other clinically similar concepts.

These properties may then be organized into property groups. A property group is a grouping of related properties. These concepts may be referenced by different names that describe the same concept. Examples of property groups might include Body Location Properties, Measurement Properties, and many other suitable property groupings. These property groups may be utilized to define which properties can qualify or modify a given clinical assertion 320 depending on the clinical assertion type. For example, types of clinical assertions 320 may include allergy, demographic, device, immunization, lab, medication, problem, procedure, physiologic, a range of other clinical assertions types, and any other suitable clinical assertion types or concepts similar to these concepts.

In general, many properties can be associated with a given clinical assertion 320. Rather than listing all possible properties, the systems and methods described herein may provide a predetermined list of properties (that includes only a subset of all possible properties). The predetermined list may be determined by the type of clinical assertion 320. For example, for a medical condition type clinical assertion 320 (e.g. problem), the predetermined list of properties may include Body Location Properties and Temporal Properties, but not Medication Properties or Demographic Properties. For example, it would make sense to say "diabetes mellitus for 5 years" since 5 years is a duration and falls within the temporal properties group. But it would not make sense to say "500 mg diabetes mellitus". Within the model, this is because 500 mg is a medication dosage and falls within the medication properties group, which is not associated with the problem type clinical assertion 320. In some embodiments, the method may include, for any given clinical assertion 320, a description of which properties will be used for coding (or any other suitable integration with an application) and how important each property is. Further, for any given clinical assertion 320, there may be a set of properties to be included in coding (or any other suitable downstream application) ordered as a priority list defining which of those properties are more important and which are less important. In some embodiments, this priority list may be used to determine which granular terms are most important and must be included in a code. In some embodiments, this priority list may be used to achieve the most granular code for any given terminology.

In some embodiments, there may be three types of property groups. These may include universal properties, common properties, and statement specific properties. In some embodiments, universal properties would apply to all clinical assertion types. Common property groups may apply to several but not all clinical assertion types. For example, in some embodiments, anatomic and temporal properties might be important to many clinical assertions types, such Problem and Procedure, but do not apply to all clinical assertion types, such as Demographic. Statement specific properties may only apply to a single clinical assertion type. For example, medication specific properties may only apply to medication type clinical assertions.

In one specific example, the following property groups may apply to the following clinical assertion types as listed below. These groups and properties demonstrate concepts and may utilize different or similar names.

| Type | Property Groups |
|---|---|
| Allergic Reaction | Universal Properties |
| | Association Properties |
| | Temporal Properties |
| | Allergy Specific Properties |
| | Precoordinated Properties |
| Demographic | Universal Properties |
| | Demographic Specific Properties |
| Device | Universal Properties |
| | Associated Device Properties |
| | Body Location Properties |
| | Temporal Properties |
| | Device Specific Properties |
| | Precoordinated Properties |
| Imaging | Universal Properties |
| | Association Properties |
| | Temporal Properties |
| | Immunization Specific Properties |
| | Precoordinated Properties |
| Lab | Universal Properties |
| | Association Properties |
| | Measurement Properties |
| | Temporal Properties |
| | Precoordinated Properties |
| Medication | Universal Properties |
| | Temporal Properties |
| | Medication Specific Properties |
| | Precoordinated Properties |
| Condition | Universal Properties |
| | Association Properties |
| | Body Location Properties |
| | Measurement Properties |
| | Temporal Properties |
| | Precoordinated Properties |
| Procedure | Universal Properties |
| | Association Properties |
| | Body Location Properties |
| | Temporal Properties |
| | Procedure Specific Properties |
| | Precoordinated Properties |
| Physiologic | Universal Properties |
| | Association Properties |
| | Body Location Properties |
| | Measurement Properties |
| | Temporal Properties |
| | Physiologic Function Specific Properties |
| | Precoordinated Properties |

Figure 4:
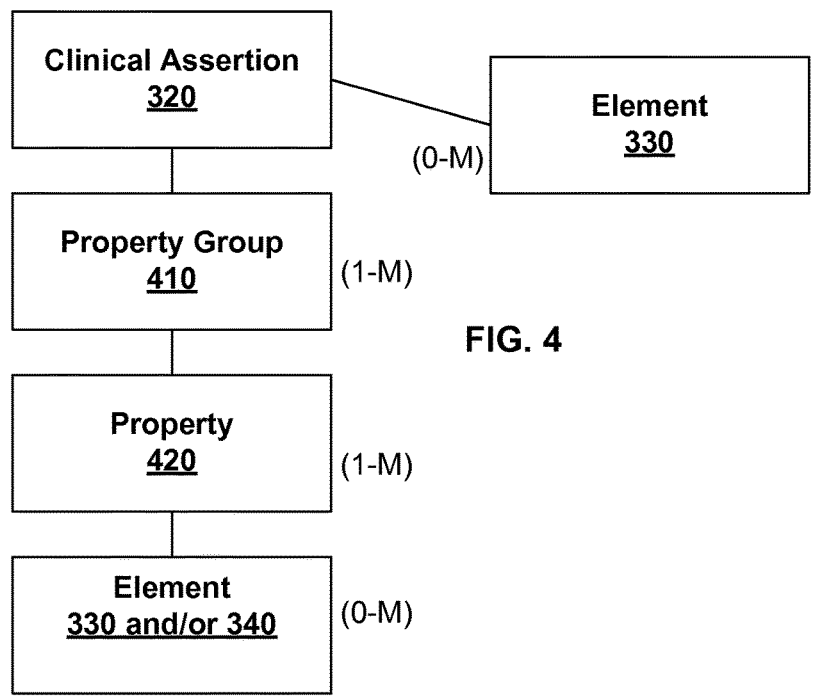
FIG. 4 illustrates one embodiment of relationships between clinical assertions, property groups, properties, and elements.

FIG. 4 illustrates the relationships between clinical assertions 320, property groups 410, properties 420 and elements 330/340, according to various embodiments. As shown, a given clinical assertion 320 may include zero to many ([0-M]) elements 330 as children of the clinical assertion (i.e. clinical assertion elements 330A) and/or may include one to many ([1-M]) property groups 410 that apply to the given clinical assertion type. Each property group 410 may include one to many ([1-M]) properties 420 within each property group 410. Additionally, properties 420 themselves may have elements 330 and/or 340. As shown in FIG. 3, each property 420 may also include zero to many ([1-M]) elements 330 as children of the property 420. As an example the property code, which is in the Universal property group, may be modified by elements 330 such as the type of code (e.g. ICD-9) and the value of the code (e.g. 250.00). The property date may be modified by elements 330 such as day, month, and year or may use a common data type to represent date. Cardinality is listed for demonstration purposes and may be different for a given property within a given property group, clinical statement type, or other context.

In some embodiments, at least one of the following properties 420 may apply to at least one of the following property groups 410. As described above, the nomenclature [x-M] references cardinality. For example, [0-1] indicates that there can be 0 to 1 elements 330 that fall within that category and [0-M] indicates that there can be 0 to many elements 330 that fall within that category. The labels listed below in this specific example, such as "notCurrentIndicator" or "primaryTerm", may be formatted or named in any other suitable fashion to represent these concepts and/or other similar concepts.

| Universal Property Groups | |
|---|---|
| Universal Properties (implemented as attributes) | [0-1] notCurrentIndicator |
| | [0-1] notExperiencedIndicator |
| | [0-1] notDefinitiveIndicator |
| | [1-1] parseMode |
| | [0-1] sentenceIdReference |
| Universal Properties (implemented as tags) | [1-1] primaryTerm |
| | [0-M] descriptiveInformation |
| | [0-1] isNegated |
| | [0-1] subject -- attribute = [0-1] isFamilyMember |
| | [0-1] quantity |
| | [0-1] providerCertainty -- attribute = [0-1] value |

| Common Property Groups | |
|---|---|
| Association Properties | [0-1] associatedDevice |
| | [0-1] associatedLab |
| | [0-1] associatedPhysiologic |
| | [0-1] associatedProblem |
| | [0-1] associatedProcedure |
| Body Location Properties | [0-M] bodyLocation - elements = [0-1] bodySide, |
| | [0-M] relativeLocation, |
| | [0-1] nearbyLocation |
| Measurement Properties | [0-1] grade |
| | [0-M] severity |
| | [0-M] result |
| Precoordinated Properties | [0-M] code -- attributes = [1-1] codeValue, [1-1] codeSystem, [1-1] codeSystemName, [0-1] displayName, [0-1] phraseIdReference |
| Temporal Properties | [0-1] acuity |
| | [0-M] course |
| | [0-1] duration |
| | [0-1] periodicity |

| Common Property Groups | |
|---|---|
| | [0-1] relativeTime -- elements = [0-1] event, [0-1] timeRelationship |
| | [0-M] dateOfEvent |
| | [0-1] ageDuringEvent |
| | [0-M] temporalStatus |

| Statement Specific Property Groups | |
|---|---|
| Allergy Specific Properties | [0-1] reactionType |
| | [0-1] reactionCategory |
| Demographic Specific Properties | [0-M] id |
| | [0-1] birthDate |
| | [0-1] deathDate |
| | [0-1] gender -- attribute = [0-1] value (enumerated: male, female, transgender) |
| | [0-1] name |
| | [0-1] race |
| | [0-1] ethnicity |
| | [0-M] patientCharacteristic |
| | [0-1] age |
| Device Specific Properties | [0-1] deviceStatusChange |
| Medication Specific Properties | [0-1] dose |
| | [0-1] form |
| | [0-1] isSchedulePrn |
| | [0-1] schedule |
| | [0-1] schedulePrnCondition |
| | [0-1] route |
| | [0-1] medicationStatusChange |
| Procedure Specific Properties | [0-M] result |
| | [0-1] procedureMaterial |

Indicators within a Clinical Model

In some embodiments, labels may be used to emphasize important context for a clinical assertion 320. In some embodiments, labels describing important content for retrieval, also known as indicators, may be emphasized with a special name or characteristic to suggest they describe critical content. In some embodiments, indicators may be used as a warning for downstream applications or users to avoid errors in retrieval of information. In some embodiments, possible indicators include that a clinical assertion 320 is historical rather than current (occurred in the past), was not experienced by the subject of the narrative content (did not occur to the patient), and is not definitive (may or may not have occurred). In some embodiments, the indicators and indicator function may have different names but convey similar meaning.

In some embodiments, a historical rather than current indicator may support subsequent usage of the data to avoid misinterpretation. One example of usage of a historical rather than current indicator may be a clinical assertion 320 of coronary artery bypass surgery in the past surgical history section of a narrative note. In this example, it may be important to convey that an operation was asserted within the text, but the patient is not currently undergoing the operation. Another example of usage of a historical rather than current indicator is "history of lung cancer". In this example, it may be important to convey that the clinical assertion 320 of lung cancer is historical and may not be currently relevant. Understanding whether an event is current may be challenging. As an example, "history of diabetes" typically refers to a patient who actively has diabetes, while "history of cancer" frequently refers to a patient who had cancer in the past, where cancer may or may not be an active problem.

In some embodiments, a not experienced indicator may support subsequent usage of the data to avoid misinterpretation. One example of usage of a not experienced indicator may be a clinical assertion of heart attack that is referenced as occurring in the family history, for example a father who died of heart attack. In this example, it may be important to convey that heart attack was asserted within the narrative, but the subject of the narrative, the patient, is not asserted to have had a heart attack. Another example of usage of a not experienced indicator would be a narrative of "patient denied fever". In this example, it may be important to convey that although fever is asserted, the concept is negated and was not experienced by the subject of the narrative content.

In some embodiments, a not definitive indicator may support subsequent usage of the data to avoid misinterpretation. One example of usage of a not definitive indicator may be a clinical assertion of rule out deep vein thrombosis. In this example, it may be important to convey deep vein thrombosis was asserted, but is not a certainty. Another example of usage of a not definitive indicator would be "possible lung cancer". In this example, it may be important to convey that the provider is asserting that lung cancer is a possibility, but not asserting that it is a certainty.

Parsing the Clinical Assertion into Individual Components

Figure 5:
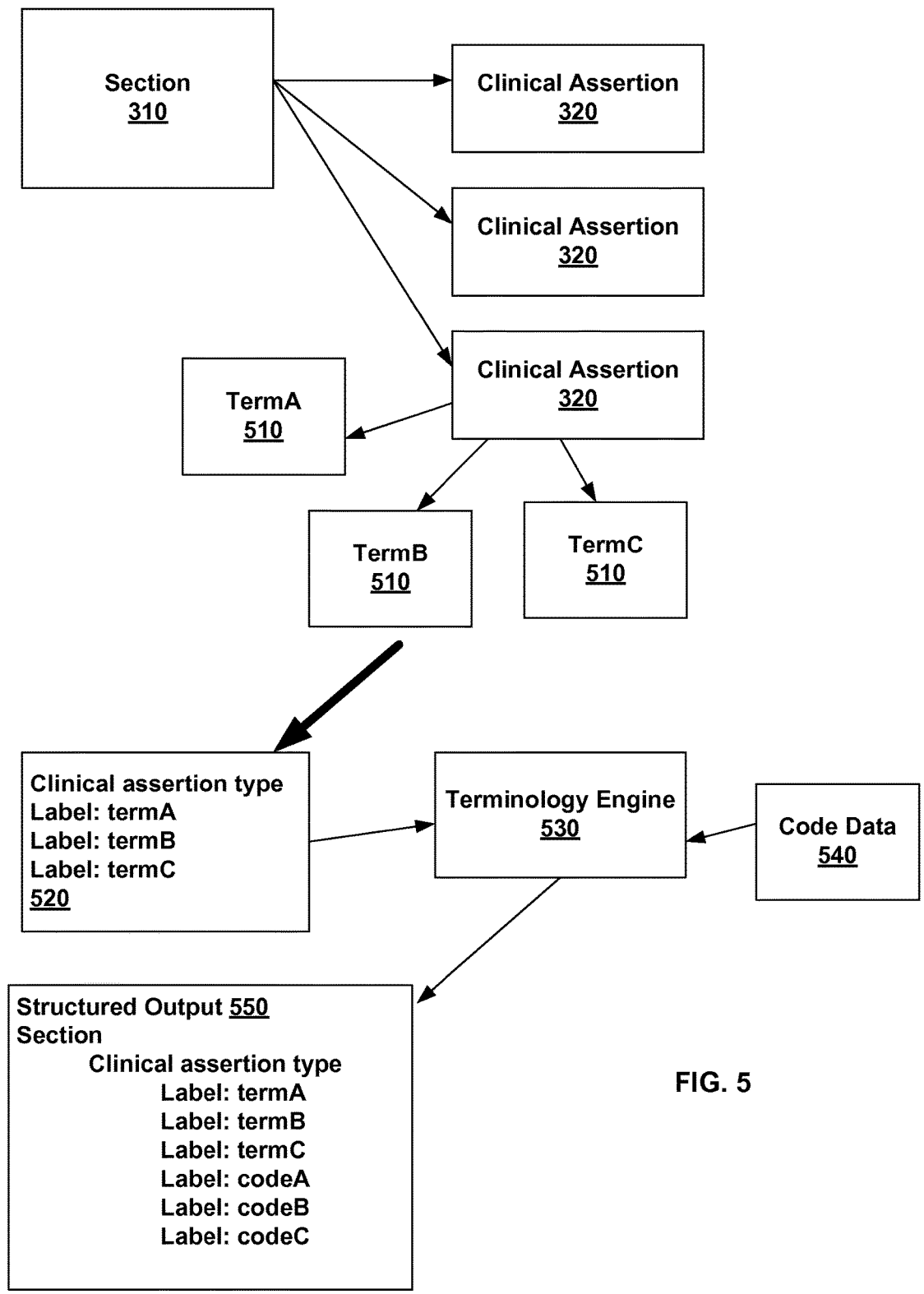
FIG. 5 illustrates transforming narrative content into structured output that defines where individual information resides within the output, according to various embodiments.

FIG. 5 illustrates the transformation of data during identify section step 230 and/or extract step 240. As shown an identified section 310 of narrative content is transferred into structured output 550 that defines where individual information resides within the output. include the steps of receiving content 210; scanning 220 the narrative content using a natural language processing (NLP) engine to identify a clinical assertion; and identifying sections 230. The identify section step 230, can include parsing a Section 310 into clinical assertions 320 and then parsing the clinical assertion 320 into individual components (terms 510). During this process, A clinical model is used to annotate the individual terms 510 within the clinical assertion 320 by associating at least one of the individual components with a label selected from a predetermined list of labels within the clinical model. This results in labeled data 520. The labeled data is provided to a terminology engine 520, which is optionally included in section identifier 130 or section extractor 140. Terminology engine 530 uses code data 540, which may be stored in clinical model storage 150. The terminology engine assigns codes to the terms using the identity of the terms and the assigned labels. As illustrated by FIG. 5, the step of parsing the clinical assertion into individual components may include parsing the clinical assertion into its individual components that include, for example, termA, termB, and termC.

Figure 6A:
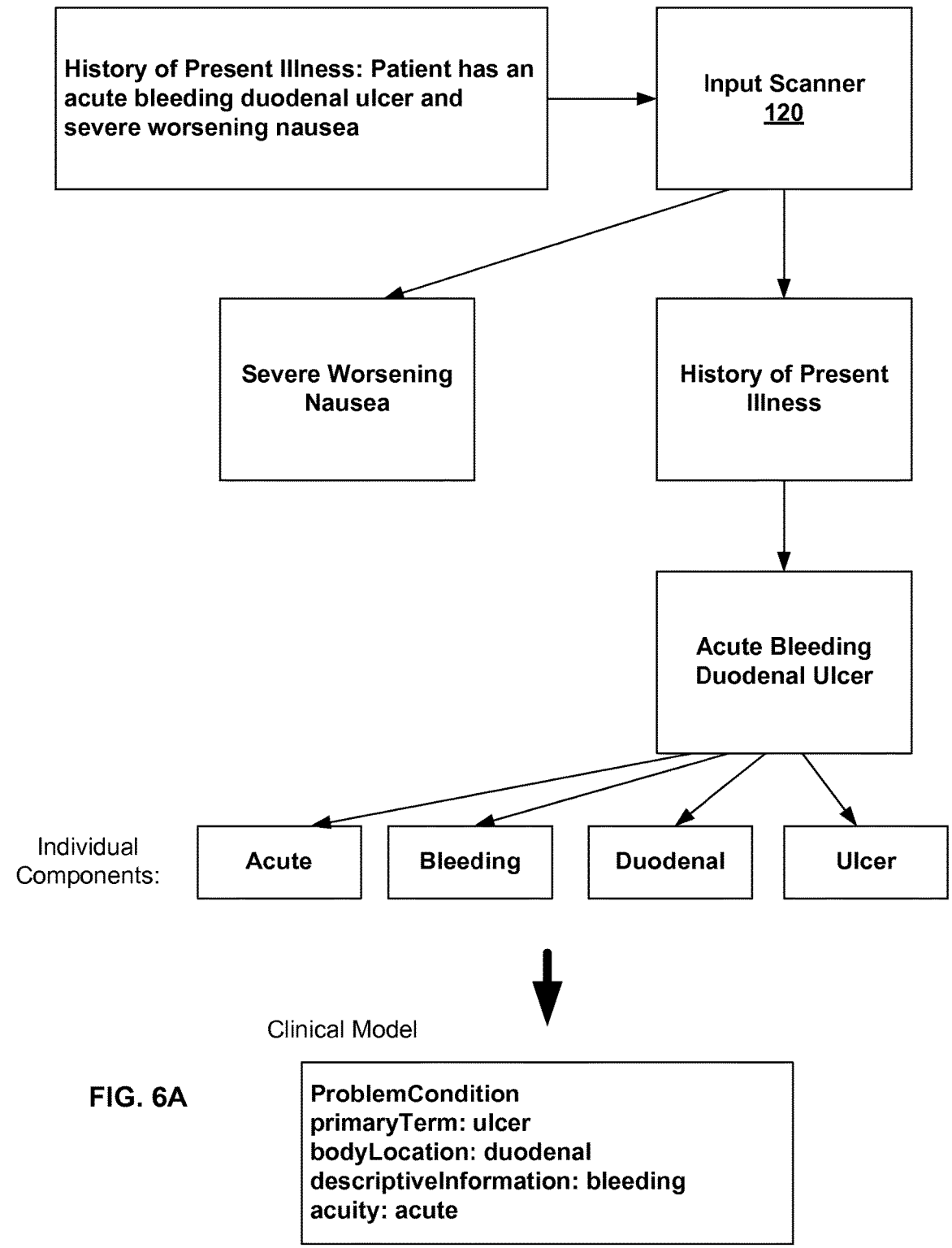
FIGS. 6A and 6B illustrate, by way of example, transforming narrative content into structured output that defines where individual information resides within the output, according to various embodiments.
Figure 6B:
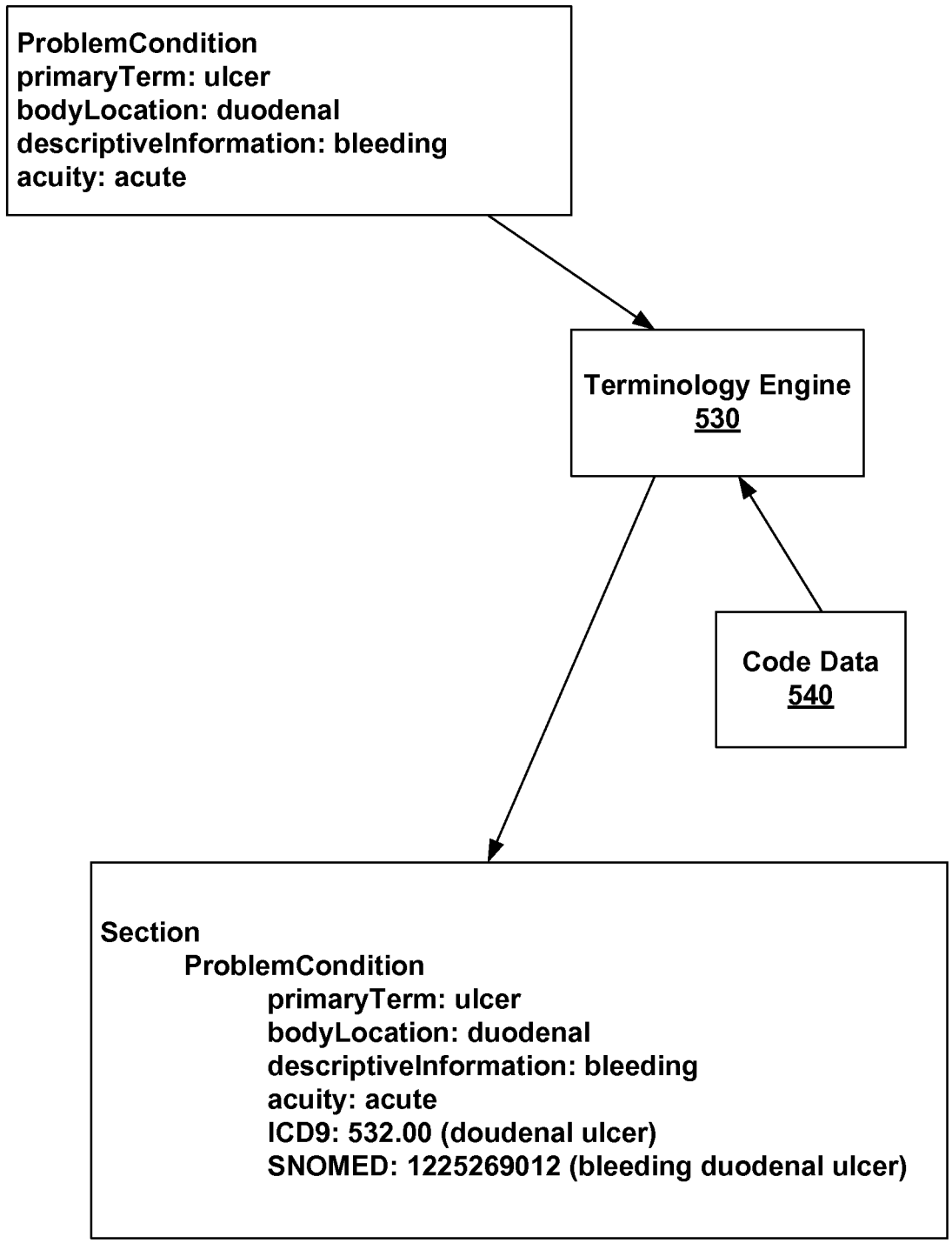

FIGS. 6A and 6B illustrate an example of the data transforms illustrated by FIG. 4. The methods described herein for transforming a specific narrative content include the steps of receiving narrative content 210; and scanning 220 the narrative content using a natural language processing (NLP) engine to identify a clinical assertion 320. In identify section step 230 and extract step 240 clinical assertions 320 are parsed into individual components; and a clinical model is used to annotate the individual components within the clinical assertion by describing at least one of the individual components with a label. As shown in FIG. 6A, the specific narrative content includes: History of Present Illness: Patient has an acute bleeding duodenal ulcer and severe worsening nausea. As shown, the narrative content is scanned to identify clinical assertions 320. In this embodiment, a section 310 and multiple clinical assertions 320 may be identified. For example, the section 310 is "History of Present Illness", the first clinical assertion 320 is "acute bleeding duodenal ulcer", and the second clinical assertion 320 is "worsening severe nausea". As shown in FIG. 6A, the clinical assertions 320 may be parsed into their individual components. Only the parsing of the first clinical assertion 320 is shown for clarity. For example, the first clinical assertion 320 can be parsed into its individual components including "acute", "bleeding", "duodenal", and "ulcer". In the step of using a clinical model to annotate the individual components within the clinical assertion 320 by describing individual components with a label, the individual components may be labeled as such: "acuity: acute", "descriptiveInformation: bleeding", "bodyLocation: duodenal", and "primaryTerm: ulcer". Furthermore, the clinical assertion type may be labeled as "problem" to describe a clinical problem. The labels in this specific example, such as "acuity" or "problem", may be formatted or named in any other suitable fashion to represent these concepts and/or other clinically similar concepts. This may be represented in XML through tagged elements and attributes.

Mapping to One or More Codes within at Least One Terminology Standard.

In some embodiments, as shown in FIGS. 5, 6A, and 6B, the method may further include the step of mapping a whole or part of the labeled individual components to one or more codes within at least one terminology standard. In some embodiments, the method further includes the step of passing the labeled individual components to a terminology engine. In some embodiments, the methods may further include the step of providing the annotated components to a terminology engine for mapping to a lexicon or ontology.

In some embodiments, the providing step further comprises providing postcoordinated content to be mapped to corresponding codes, wherein the postcoordinated content comprises a set of elements prioritized based on the clinical assertion type and clinical model labels, as shown in FIGS. 5, 6A, and 6B.

In some embodiments, the mapping step is performed by terminology engine 530. In some embodiments, the corresponding codes align with a lexicon. In some embodiments, the lexicon may include at least one of ICD-9, ICD-10, LOINC, CPT, and RxNorm. In some embodiments, the corresponding codes align with a language that incorporates associations between terms. In some embodiments, the corresponding codes align with an ontology. In some embodiments, the corresponding codes align with SNOMED. In some embodiments, one or more other lexicons or ontologies may be used to represent concepts.

Matching a (Prioritized) Set of Properties to at Least One Code within a Terminology In some embodiments, the method further includes the step of utilizing an algorithm to match a clinically important set of properties within a clinical assertion 320 to at least one code within a terminology. In some embodiments, the algorithm uses labels within a clinical model to determine which properties are most important for a given clinical assertion type. In some embodiments, the algorithm uses permutations of postcoordinated elements of a clinical assertion 320, first attempting to find a match based on all mapped elements, subsequently attempting to find a match based on the most important elements based on the clinical model, and subsequently removing the least important elements based on the clinical model, until a coding match is found for the most important subset of elements within a clinical assertion 320 to a given terminology. As an example, the phrase "severe acute bleeding duodenal ulcer" may contain five unique terms, which in this case correspond to the five words in the phrase. A highly granular controlled vocabulary, such as the proprietary Intelligent Medical Objects (IMO) vocabulary, may have a code for "acute bleeding duodenal ulcer" whereas SNOMED and ICD-9 may only have the less specific code for "bleeding duodenal ulcer". SNOMED may also have a code for "acute duodenal ulcer". The clinical model labels and priority of importance within a given clinical assertion type may allow the system to select the most granular match within a given terminology and to select between two equally granular matches based on importance of items determined by the clinical model labels. In this example, the map may result in the IMO code for "acute bleeding duodenal ulcer" and the SNOMED, ICD-10, and ICD-9 codes for "bleeding duodenal ulcer".

In some embodiments, the method may further include the step of prioritizing a set of the individual elements based on a predetermined priority list, wherein the predetermined priority list differs according to a concept (or clinical assertion) type and deriving codes based on a prioritized permutation of the individual elements, wherein the prioritized permutation of the individual elements is the highest priority permutation that is recognized within a given coding system. In some embodiments, the codes are derived from a terminology engine. For example, for any given clinical assertion 320, there may be a set of properties to be included in coding ordered as a priority list defining which of those properties are more important and which are less important. For example, the primary term property (e.g. primaryTerm) may be more important than the descriptive information property (e.g. descriptiveInformation). The body location property (e.g. bodyLocation) may be more important than acuity (e.g. acuity). As one specific example, the ordered list for the clinical assertion type labeled "problem" may read 1) primaryTerm, 2) bodyLocation, 3) bodySide, 4) acuity. Therefore, as an example, the problem type clinical assertion of "left heel ulcer" may be prioritized as 1) primaryTerm: ulcer, 2) bodyLocation: ulcer, and 3) bodySide: left. Over time, properties may be added, taken away, or rearranged in this priority list. The priority list may be applied to all concepts, only to concepts within a given clinical statement type, or only to specific concepts. The systems and methods described herein may have enough flexibility that the algorithm which connects the postcoordinated output to a terminology engine (or other application) can be easily modified. In some embodiments, the step of deriving codes based on a prioritized permutation of the individual elements may further include repeatedly sending various permutations of terms to a terminology engine, or other application, until a match is found. Consider the following example. A priority list for a clinical assertion may read: 1) primaryTerm, 2) bodyLocation, 3) bodySide, 4) acuity. The method or system may first send terms 1, 2, 3, and 4 to the terminology engine. If there is no match, i.e. there is no code found for that string of terms, the method or system may then send terms 1, 2, and 3. If still no match terms 1 and 2 may be sent. Again, if there is still no match, just term 1 may be sent. Alternatively 1, 2, 3, and 4 may first be sent; followed by 1, 2, and 3; and then 1, 2, and 4; and then 1, 3, and 4; and through all the different permutations until a match is found. Over time, the algorithm may be changed to optimize results. In some embodiments, the same algorithm may apply to all clinical assertion types and it may not necessarily have a different algorithm for each clinical assertion type. The labels listed above in this specific example, such as "primaryTerm", "bodyLocation", "bodySide", and "acuity", may be formatted or named in any other suitable fashion to represent these concepts and/or other clinically similar concepts.

Consider the specific example. A medical condition type (e.g. problem) clinical assertion such as "acute bleeding duodenal ulcer", as illustrated in FIGS. 6A and 6B, may have several mapping options for SNOMED. The terminology engine may return a code for acute duodenal ulcer, bleeding duodenal ulcer, and duodenal ulcer as well as other possible options. In some embodiments, it may label bleeding duodenal ulcer as the preferred term. In some embodiments, the system may be adjustable in terms of how many codes for any given code system are actually incorporated within the output. In some embodiments, there may be multiple choices for SNOMED (with one preferred choice), for example, but only one choice for ICD-9, and they may code to different permutations. As shown in FIG. 6B, the code returned for SNOMED is 1225269012 for bleeding duodenal ulcer, while the code returned for ICD-9 may be 532.00 for duodenal ulcer.

Consider another example. The phrase "open left femur fracture" may be mapped to the postcoordinated representation "problem: primaryTerm fracture, bodyLocation femur, bodySide left", descriptiveInformation open. A highly granular ontology such as SNOMED may include a code for open femur fracture, but may not have left femur fracture since SNOMED does not code sidedness. A less granular lexicon such as ICD-10 may happen to include a more granular code for left femur fracture since that lexicon incorporates body side. A common practice in code matching is to start with a granular ontology, such as SNOMED, and map to less granular lexicons such as ICD-10. In this case, the more granular code for left femur fracture would have been lost using common practices. Instead mapping to each controlled vocabulary using a permutation of postcoordinated terms allows the most granular and highest priority match.

CONCLUSION

Various embodiments of systems and methods for processing unstructured data are provided herein. Although much of the description and accompanying figures generally focuses on systems and methods that may be utilized with patient data, in alternative embodiments, systems and methods of the present invention may be used in any of a number of systems and methods.

The systems and methods described herein may process source data, such as narrative notes, into key components that are highly annotated for further use. For example, a physician's narrative note may read "History of Present Illness (HPI): This is a 78 year old woman with a history of coronary disease and diabetes, who presents complaining of shortness of breath. The patient described chest tightness, fever, dyspnea, nausea, and epigastric pain." With natural language processing (NLP), concepts may be understood in context. For example, the concepts, or clinical assertions, of "78 year old woman", "coronary disease", "diabetes", "shortness of breath", "chest tightness", "fever", "dyspnea", "nausea", and "epigastric pain" may be identified by the NLP engine. Information regarding temporal relationship or other context may further be provided by the NLP engine. These concepts may be further grouped or tagged. For example, "shortness of breath" may be tagged as a chief complaint (CC), or something clinically similar; "coronary disease" and "diabetes" may be tagged as past medical history (PMH), or something clinically similar; and "chest tightness", "fever", "dyspnea", "nausea", and "epigastric pain" may be tagged as history of present illness (HPI), or something clinically similar. Each of these items may be described with modifers or qualifiers. For instance, diabetes may be associated with the qualifier "type 2" or the modifer "no". Modifiers change the meaning of the clinical assertion, or clinical statement, where the no diabetes is significantly different than diabetes. The postcoordinated elements within a clinical statement, such as "diabetes mellitus" and "no" may be further annotated by a clinical model. The clinical model may use the clinical assertion type to define which labels are appropriate for annotation. For example, a problem type of clinical assertion may have a set of labels associated that include items such as severity and negation. The term "severe" associated with "diabetes mellitus" may be labeled as "severity: severe" or a similar representation in XML. Another clinical assertion type such as medication may have a different set of labels available, such as dose, schedule, or other suitable concepts clinically similar to these terms. The naming convention of the property is less important than the meaning. For example, medication schedule, whether called frequency, periodicity, or schedule, is materially the same.

In some embodiments, the structured output 550 may be formatted in a specialized XML format. In some embodiments, the output or a transformed representation of the output may be in the format of Clinical Document Architecture (CDA), Continuity of Care Record (CCR), Continuity of Care Document (CCD) format, or any other suitable format. In some embodiments, the output format is green CDA. In some embodiments, the green CDA schema compliant format may be transformed into CDA using an extensible stylesheet language transformation (XSLT). In some embodiments, unstructured data extensively processed can be used to partially or fully populate a HL7 version 2, HL7 version 3 or subsequent version CDA document. In some embodiments, the structured data are configured to be compatible with at least one of health information exchanges (HIEs), EHR, personal health record, data warehouse, and/or any other suitable storage, transfer, or transformation system.

In some embodiments, the NLP engine and clinical model output are ordered within a schema to support integration with data storage, data mining, data transformation, or other downstream applications. In some embodiments, the downstream application uses data mining. In some embodiments, a data mining engine is configured to process the relationships between the plurality of concepts and the aggregations of the plurality of concepts and to identify associations and correlations in the data set. Data mining can be defined as data processing using sophisticated data search capabilities and statistical algorithms to discover patterns and correlations in large databases or data sets, for example electronic health record, health information exchange, or data warehouse databases. Data mining may be used to discover new meaning in the data. In some embodiments, the data mining engine is the component that "learns" the associations. For example, based on the data set for a plurality of patients, the data mining engine may determine that diabetes is commonly referenced related to high blood glucose. In some embodiments, data mining may be used to improve the NLP engine. In some embodiments, data mining may be used to improve a downstream application. In some embodiments, data mining may be part of a downstream application. In some embodiments, data mining may be used to power a downstream application. In some embodiments, data mining may form the majority of a downstream application.

The examples and illustrations included herein show, by way of illustration and not of limitation, specific embodiments in which the subject matter may be practiced. Other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for transforming narrative content into structured output, the method comprising the steps of:
receiving narrative content;
scanning the narrative content using a natural language processing engine to transform the narrative content into a plurality of concepts within a plurality of distinct contexts;
parsing at least one of the plurality of concepts into individual elements;
annotating an individual element of the individual elements with a label within a clinical model;
prioritizing the individual elements based on a predetermined priority list, wherein the predetermined priority list differs according to a concept type; and
deriving codes based on a prioritized permutation of the individual elements, wherein the prioritized permutation of the individual elements is a highest priority permutation that is recognized within a given terminology.

2. The method of claim 1, wherein the codes are derived from a terminology engine.

3. The method of claim 1, wherein the annotating step comprises describing at least one of the individual elements with a label selected from a predetermined list of labels within the clinical model, wherein the predetermined list of labels differs according to a concept type.

4. A method for transforming narrative content into structured output, the method comprising the steps of:
receiving narrative content;
scanning the narrative content using a natural language processing engine to identify a clinical assertion;
parsing the clinical assertion into individual elements; and
describing at least one of the individual elements with a label within a clinical model, wherein the label emphasizes context for a clinical assertion.

5. The method of claim 4, wherein the label indicates that the individual element described by the label influences retrieval and usage by a subsequent application.

6. The method of claim 4, wherein the label indicates that the individual element described by the label influences retrieval and usage by a subsequent user.

7. The method of claim 4, wherein the label indicates that the individual element described by the label influences retrieval and usage by a software development kit.

8. The method of claim 4, wherein the label comprises a special name or characteristic to provide that the individual element described by the label influences retrieval and usage.

9. The method of claim 4, wherein the label indicates that the clinical assertion is historical rather than current.

10. The method of claim 4, wherein the label indicates that the clinical assertion was not experienced by the subject of the narrative content.

11. The method of claim 4, wherein the label indicates that the clinical assertion should be considered but may not have occurred.

* * * * *